ус008682424B2

(12) United States Patent
Tsoglin et al.

(10) Patent No.: US 8,682,424 B2
(45) Date of Patent: Mar. 25, 2014

(54) NONINVASIVE MULTI-CHANNEL MONITORING OF HEMODYNAMIC PARAMETERS

(75) Inventors: Alexander Noson Tsoglin, Hadera (IL); Arkady Hanon Margolin, Hadera (IL)

(73) Assignee: DST Delta Segments Technology, Inc., Birmingham, AL (US)

( * ) Notice: Subject to any disclaimer, the term of this patent is extended or adjusted under 35 U.S.C. 154(b) by 2052 days.

(21) Appl. No.: 10/566,026

(22) PCT Filed: Jul. 29, 2004

(86) PCT No.: PCT/IL2004/000696
§ 371 (c)(1),
(2), (4) Date: Dec. 26, 2006

(87) PCT Pub. No.: WO2005/010640
PCT Pub. Date: Feb. 3, 2005

(65) Prior Publication Data
US 2008/0009757 A1     Jan. 10, 2008

(30) Foreign Application Priority Data

Jul. 31, 2003  (IL) .......................................... 157199

(51) Int. Cl.
*A61B 5/02*     (2006.01)
(52) U.S. Cl.
USPC ........... 600/547; 600/481; 600/500; 600/504; 600/506
(58) Field of Classification Search
USPC ......................................... 600/481–528, 547
See application file for complete search history.

(56) References Cited

U.S. PATENT DOCUMENTS

| 3,651,318 | A | 3/1972 | Czekajewski |
| 3,726,269 | A | 4/1973 | Webster, Jr. |
| 3,915,155 | A | 10/1975 | Jacobson et al. |
| 4,450,527 | A | 5/1984 | Sramek |
| 4,671,295 | A | 6/1987 | Abrams et al. |
| 5,309,917 | A | 5/1994 | Wang et al. |

(Continued)

FOREIGN PATENT DOCUMENTS

WO     WO 03/003920     1/2003

*Primary Examiner* — Michael Kahelin
*Assistant Examiner* — Karen Toth
(74) *Attorney, Agent, or Firm* — Roach Brown McCarthy & Gruber, P.C.; Kevin D. McCarthy

(57) ABSTRACT

A method and system for measuring the electrical impedance of sections of a living body. The measurement is carried out utilizing a plurality of electrodes each of which is disposed on a section of the living body, where the electrodes are capable of applying an electrical current through at least one probed section, and measure the electrical voltage over the probed section. The voltages over the probed sections are measured and the impedances (Z(t)) and their changes (ΔZ(t)), and the resistances R(t) and their changes (ΔR(t)), are calculated, by considering the electrical current distortion components resulting from the electrical currents flowing in the other sections which are not probed, utilizing an electrical model based on the distribution of the electrical currents through the body sections. The measuring is preferably performed by applying an electrical current through the probed section of the living body via a pair of electrodes, and measuring the electrical voltage over the probed section and over the other sections, applying an electrical current through one or more of the other sections and at each instance measuring the electrical voltage over the other sections; and calculating the impedance and resistance and the changes utilizing the measurements and the applied currents, according to the electrical model.

16 Claims, 15 Drawing Sheets

(56) References Cited

U.S. PATENT DOCUMENTS

| | | |
|---|---|---|
| 5,529,072 A | 6/1996 | Sramek |
| 5,720,296 A * | 2/1998 | Cha ............................. 600/554 |
| 5,735,284 A * | 4/1998 | Tsoglin et al. ................ 600/513 |
| 6,014,583 A | 1/2000 | Nakagawara et al. |
| 6,161,038 A * | 12/2000 | Schookin et al. ............. 600/519 |
| 7,783,345 B2 * | 8/2010 | Skrabal et al. ................ 600/547 |

\* cited by examiner

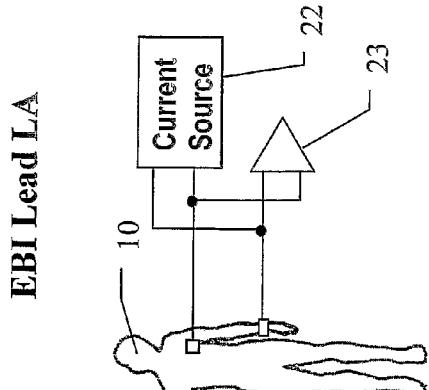
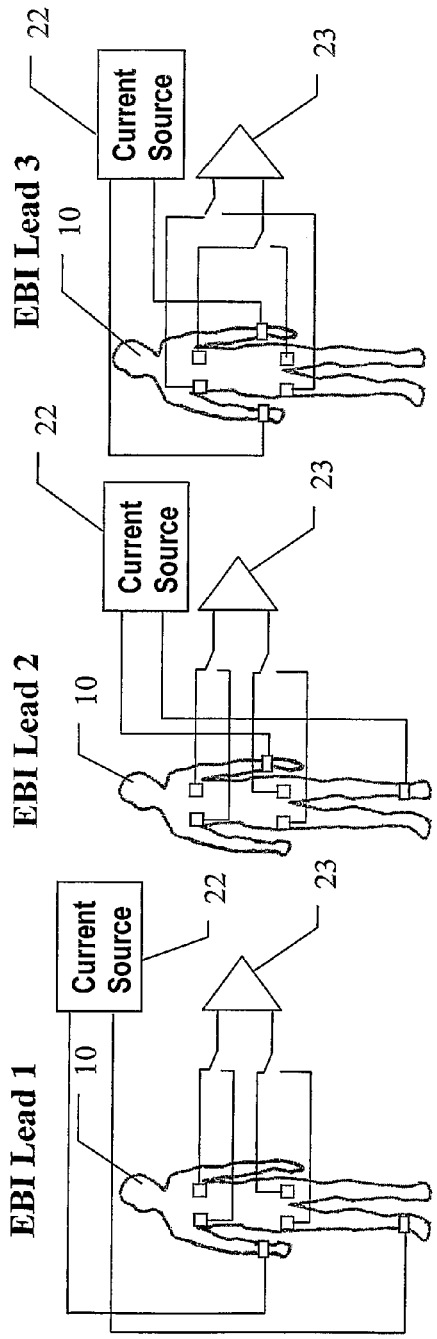
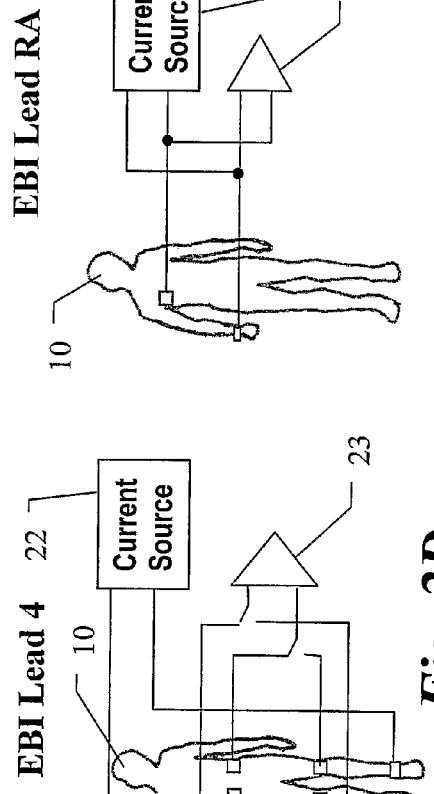

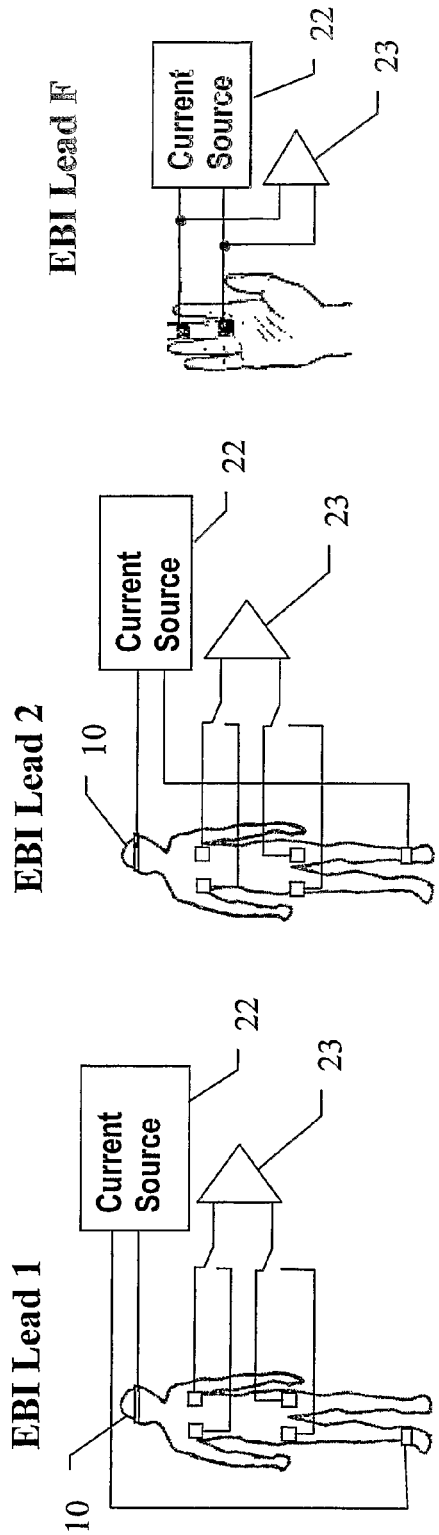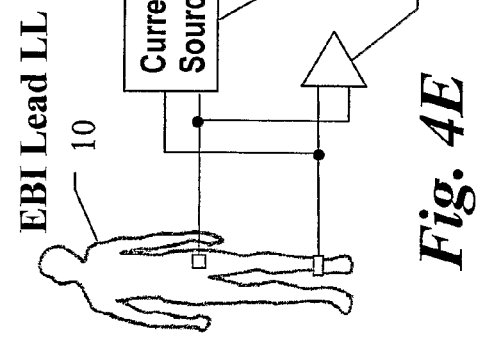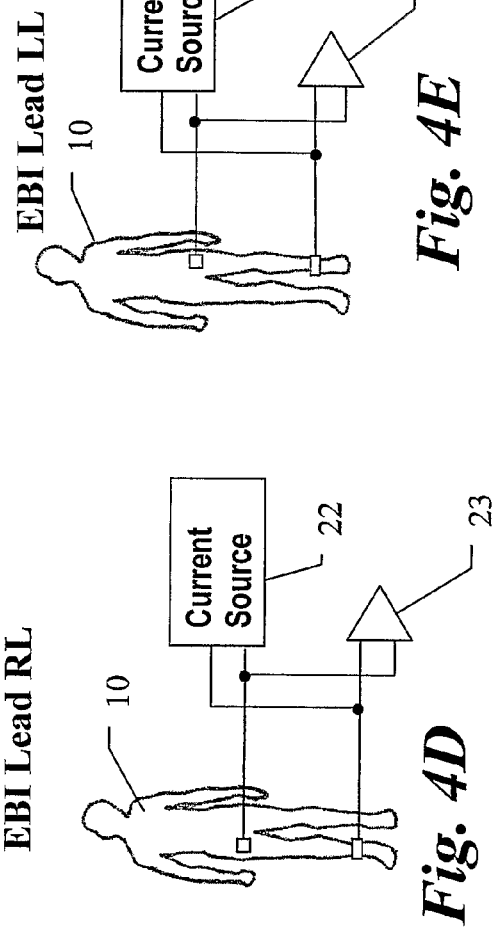

NONINVASIVE MULTI-CHANNEL MONITORING OF HEMODYNAMIC PARAMETERS

FIELD OF THE INVENTION

The present invention relates to noninvasive monitoring of hemodynamic parameters of organs of the living body. More particularly, the invention relates to a method and apparatus for measuring pulmonary, systematic blood and peripheral flow parameters based on electrical impedance measurements.

BACKGROUND OF THE INVENTION

The ability of medical practitioners to obtain an accurate and substantially continuous assessment of a patient's cardiac performance, and to assess system blood flow of systemic (Left side of the heart) and pulmonary (right side of the heart) circulation separately is very important.

In the current medical practices and particularly in Intensive Care Units, for instance, different devices are used for measuring the right and the left functionality of the heart during the treatment of cardiac patients. Invasive methods are usually used for obtaining measurements of the hemodynamic parameters of the right side of the heart, and noninvasive methods are usually used for measuring the hemodynamic parameters of the left side of the heart.

Some of the known invasive methods for measurement of pulmonary blood flow are: the indicator dilution methods; the blood flow determination by catherization, also known as the Swan Ganz methods; and blood flow determination by simultaneous blood sampling (from a vein and an artery coincident with measurement of oxygen consumption), also known as the Fick methods. The most widely used methods are the Swan Ganz, as described, for example, in U.S. Pat. Nos. 3,915,155, 3,726,269 and 3,651,318. The invasive methods require inserting a measuring device into the patient's body, such as a catheter in the throat, and present numerous disadvantages to both patient and physician. The patient must often endure substantial pain and discomfort and the physician must perform a relatively complicated procedure which occasionally involves exposure to the risks of contact with infectious blood.

Right heart catheterization allows precise assessment of dynamics in the right side of the heart and pulmonary arterial bed. However, this technique provides only indirect information about the left side of the heart, and in the vast majority of cases, the left side of the heart is more important in diagnostics, particularly in heart disease patients.

The noninvasive methods that are currently used for measuring systematic (left ventricle) blood flow represent a major advancement, but still have significant shortcomings. Most of those methods are based on ultrasound measurements, phonocardiography, or electrical impedance in order to calculate hemodynamic parameters, which are not adequately used to obtain a precise assessment of hemodynamic parameters of separate bodily sections.

Consequently, for many years work has been underway to develop less invasive apparatus and methods for monitoring cardiac output. For example, as an alternative to catherization methods, Doppler ultrasound techniques have been adapted to measure the velocity of blood flow. The Doppler ultrasound measurements of the ascending aorta, either externally (from the suprasternal notch) or internally (from within the trachea) can be used as a measure of cardiac output. But this technique requires determining of the diameter of the vessel, its flow profile, and the angle of the ultrasound beam relative to the vessel, in order to yield accurate results.

U.S. Pat. No. 4,671,295 describes an implementation of such methods, wherein an ultrasound transducer is mounted on the tip of an endotracheal tube so that Doppler measurements of blood flow from a point (pulse wave mode) or path (continuous wave mode) along the ultrasound beam can be measured. However, this method requires carrying out multiple measurements within the blood vessel, a priori knowledge of the blood flow pattern and cross-sectional area of the vessel and the relative angulation of the blood vessel. In addition, the accuracy of the measurements is highly dependent upon the exact placement of the transducer. These drawbacks have resulted in the slow adoption of Doppler ultrasound cardiac output techniques.

There are two noninvasive methods of electrical impedance measurements, the thoracic region and whole body methods, which are also known in the art.

These methods use an electrical impedance measurement apparatus which employs two excitation electrodes, situated at two ends of the measured section, between which a low level current is passing. Two sense electrodes, situated at intermediate locations, are used for sensing the tissue impedance. The electrical current predominantly flows through materials with high conductivities, such as blood. Smaller portions of the electrical current flow through the muscles, which have an intermediate conductivity, while another portion of the electrical current flows through fat, air, and bones, the conductivity of which is significantly smaller than that of either blood or muscles. Since the value of the resistance to current flow is a function of the conductivity and of the cross-sectional area of the conducting volume, volumes having a larger cross-sectional area are necessarily of lower resistance. Such deviations of the conducting volumes causes changes in the electrical impedance measured over time and in effect introduce difficulties in correlating the measured impedance with the cardiac parameters (such as stroke volume).

The noninvasive electrical impedance methods that are used for measuring the left ventricle hemodynamic parameters have the following disadvantages:

- the thoracic electrical impedance method measures both right and left ventricle blood flows together, but it is impossible to obtain separate measurements from each ventricle utilizing the prior art methods. This shortcoming decreases accuracy of the measurement of hemodynamics parameters of the left ventricle.
- the whole-body electrical impedance methods (e.g., U.S. Pat. No. 5,735,284) measures a combined impedance of the aortic blood flow (Left ventricle blood flow) and the blood flow in the peripheral organs. Therefore, the electrical impedance components, which are contributed by the blood flow via peripheral organs, introduce errors to the measurements of aortic blood flow.

For the accurate determination of the hemodynamics parameters based on electrical impedance measurement, the following problems should be resolved:

I. Electrodes Position Problems

The manner in which the electrodes are arranged on the patient's body plays an important role in increase of accuracy of hemodynamics parameter measurements. Due to various anatomical factors, the electrodes are placed over certain areas of the body in order to achieve optimal correlation between measured changes in electrical impedance and the hemodynamics parameters. Many of the electrode configurations currently in use fail to adequately take into account the paths followed by the lines of electrical potential through the thorax and thus create distortions in the hemodynamic parameters measurement.

In electrical impedance measurement devices, the excitation and sensing electrodes are placed in proximity on the patient's chest, which as results the electrical current travels along different paths and through many different tissue interfaces. It is therefore impossible to know the exact path of the electrical current through the patient's chest. Another problem with thoracic electrical impedance has been correcting the cyclical changes of the gas volume inside the lungs. The lung impedance is directly proportional to the volume of air in the lung, i.e., as air volume increases, impedance increases, which results in distortions of the $\Delta Z$ signal. The relationship between the change of the impedance value ($\Delta Z$) and change in the volume of air in the lung is nearly linear under most circumstances and mainly depends on the electrodes' location and chest size.

Additional disadvantages of the bioimpedance measurement methods mentioned above are the problems in the accuracy of the impedance signal measurement, which are common for all the bioimpedance methods.

II. Excitation Current Distortion Problems:

To obtain an accurate measurement of the base impedance Z and of the impedance changes $\Delta Z$, one must take the redistribution of the current into body organs that are not supposed to be measured into account.

III. Signal to Noise Ratio Problem

There is always an ongoing effort to increase the Signal to Noise Ration (SNR) of the measured impedance signal, namely, to increase the sensitivity by increasing the SNR.

Simultaneously measurement of hemodynamic parameters of different organs and sections of the living body is very important. Although there are methods, which measure hemodynamic parameters in different sections of the human body, such as described in WO 03/003920, such prior art methods measure hemodynamic parameters with less accuracy, since those methods do not take into consideration the presence of the distortions that are introduced into the measurements due to the electrical current flows of the excitation currents to the peripheral sections which are not required for the measurements. Moreover, none of the prior art methods suggests how to cancel these distortions of the measurements.

All the methods described above have not yet provided satisfactory solutions for accurately measuring the electrical impedance of distinct body sections, and for reliably obtaining the corresponding hemodynamic parameters that can be derived from such measurements.

It is an object of the present invention to provide a method and apparatus for a noninvasive multi-channel monitoring of hemodynamic parameters of distinct sections and organs of the living body.

It is another object of the present invention to provide a method and apparatus for measurement of left and right ventricle blood flows separately.

It is another object of the present invention to provide a method and apparatus for measurement of hemodynamic parameters of systemic, pulmonary and peripheral blood flows simultaneously.

It is another object of the present invention to provide a method and apparatus for a noninvasive multi-channel monitoring of hemodynamic parameters in which the distortions introduced into the measurements due to electrical currents flows through peripheral sections of the measured body are removed by considering the excitation current distortion components.

It is a further object of the present invention to provide a method and apparatus for a noninvasive multi-channel monitoring of hemodynamic parameters utilizing an electrode configuration which provides improved uniformity of field distribution within sections and organs of the measured body.

It is another object of the present invention to provide a method and apparatus for digital signal processing for increasing the accuracy and sensitivity of measurement of bioimpedance of sections and organs of measured body.

Other objects and advantages of the invention will become apparent as the description proceeds.

SUMMARY OF THE INVENTION

The following are defined as follows:
Bioimpedance—the electrical properties of a living body.
Electrical impedance signal—the electrical impedance as it changes in time.
Central hemodynamic trace—pulmonary and Systemic blood flow circulation.
lines of electrical potential—the electrical paths in the body which are due to the main blood vessels.
Tetrapolar system—a system for measuring the body impedance by concurrently utilizing a pair of excitation electrodes and a pair of sensing electrodes.
Bipolar system—a system for measuring the body impedance by concurrently utilizing a single pair of electrodes which are used for both excitation and sensing.
QRS complex—a characteristic of electrical activity of the heart.

In one aspect the present invention is directed to a method and system for measuring the electrical impedance of sections of a living body. The measurements are performed utilizing a plurality of electrodes each of which is disposed on a section of the living body, where the electrodes are capable of applying an electrical current through at least one probed section, and measure the electrical voltage over the sections, of the living body. An apparatus is used, capable of measuring the voltages over the sections and accurately calculating the impedance ($Z(t)$) and the impedance changes ($\Delta Z(t)$), the resistance $R(t)$ and the resistance changes ($\Delta R(t)$), of at least the probed section. Accurate results are obtained by considering the electrical current distortion components resulting from the electrical currents flowing in the other sections which are not probed, by utilizing an electrical model based on the distribution of the electrical currents through the sections, and by repeatedly performing the following steps:

applying an electrical current through the probed section of the living body via a pair of electrodes, and measuring the electrical voltage over the probed section and over the other sections;

applying an electrical current through one or more of the other sections and at each instance measuring the electrical voltage over the other sections; and calculating the impedance and resistance and the changes utilizing the measurements and the applied currents, according to the electrical model.

The electrodes may be applied such that at least one of the sections is associated with and inner body organ.

Optionally, the electrodes are applied such that at least four electrodes are applied to the upper and lower limbs of the body, such that at least one of the electrodes is applied to the right arm, to the left arm, to the right leg, and to the left leg, and at least four electrodes are applied to the trunk area of the measured body, such that at least one of the electrodes is applied to the upper part of the right side of the trunk, to the lower part of the right side of the trunk, to the upper part of left side of the trunk, and to the lower part of the left side of the trunk.

In a preferred embodiment of the invention the electrical impedance of sections of a living body are measured utilizing an electrical model based on the distribution of electrical currents through the sections. The electrical impedance is measured utilizing:

- a plurality of electrodes each of which is disposed on sections of the living body, where the electrodes are capable of applying an electrical current through at least one section, and measure the electrical voltage over other sections, of the living body;
- processing means capable of selecting one or more pairs of electrodes to be used as excitation electrodes and one or more pairs of electrodes to be used as sensing electrodes, capable of outputting and inputting digital signals and of processing the signals;
- a digital-to-analog converter capable of receiving digital signals from the processing means and outputting a corresponding analog signal;
- a current source capable of producing an electrical current, the magnitude of which is proportional to the amplitude of the analog signal;
- an amplifier for obtaining the signal obtained via the sensing electrodes and amplifying it;
- a switching circuitry linked to the processing means and to the current source and to the amplifier, and capable of applying the electrical current to the pair of excitation electrodes, and pick up an electrical voltage measurement via the sensing electrodes;
- providing an analog-to-digital converter for converting the amplified signal and delivering a corresponding digital signal to the processing means,
- Electrical current is applied through the at least one section via the selected pair of excitation electrodes, and at each instance the electrical voltage over the selected sensing electrodes is measured. In this way, the electrical impedance can be calculated by the processing means by utilizing the measured electrical voltages and the applied currents, according to the electrical model. The electrodes may be applied such that at least one of the sections is associated with and inner body organ.

The invention may further include utilizing a low-pass-filter for filtering the signal used as a reference for producing the electrical current. A high-pass-filter may be used for filtering the analog signal to be converted by the analog-to-digital converter, and a programmable gain amplifier controlled by the processing means may be utilized for amplifying the amplitude of the analog signal to be converted by the analog-to-digital converter. Alternatively, the analog signal to be converted by the analog-to-digital converter is filtered by the high-pass-filter and amplified the programmable gain amplifier.

The invention may further include processing the digital signal produced by the analog-to-digital converter and computing the active component of the impedance and the changes of the component, by splitting the digital signal into wave-packets, where each wave-packet includes a complete number cycles of the signal; multiplying the wave-packets by a digital sinusoidal waveform with the same frequency and phase as the signal cycles in the wave-packets; summing the results of the multiplication of a wave-packet by the digital sinusoidal waveform; storing the summation results in a memory; calculating the measured resistance by utilizing the summation results and the electrical model; filtering the measured resistance by a low-pass-filter to obtain the mean value of the measured resistance; and by subtracting the mean value from the measured resistance to obtain the changes of the measured resistance and basal resistance.

The multiplication of the wave-packets optionally comprises multiplying each wave-packet signal by itself, thereby raising it to the second power, to obtain the impedance value and it changes.

According to another preferred embodiment of the invention the electrical impedance of sections of a living body is measured utilizing an electrical model based on the spatial distribution of the sections by applying at least four electrodes to the upper and lower limbs of the measured body, such that at least one of the electrodes is applied to the right arm, to the left arm, to the right leg, and to the left leg, and by applying at least four electrodes to the trunk area of the measured body, such that at least one of the electrodes is applied to the upper part of the right side of the trunk, to the lower part of the right side of the trunk, to the upper part of left side of the trunk, and to the lower part of the left side of the trunk. At least six of the following measurements are performed:

- measuring the voltage over a right pair of electrodes applied to the upper and lower parts of the right side of the trunk, and the voltage over a left pair of electrodes applied to the upper and lower parts of the left side of the trunk, where the voltages are measured in response to a first excitation current applied via electrodes applied to the left leg and to the left arm;
- measuring the voltage over the right pair of electrodes, and the voltage over the left pair of electrodes, where the voltages are measured in response to a second excitation current applied via electrodes applied to the right leg and to the right arm;
- measuring the voltage over an upper pair of electrodes applied to the right and to the left sides of the upper part of the of the trunk, and the voltage over a lower pair of electrodes applied to the right and to the left sides of the lower part of the trunk, the voltages are measured in response to a third excitation current applied via electrodes applied to the right leg and to the left leg;
- measuring the voltage over the upper pair of electrodes, and over the lower pair of electrodes, the voltages are measured in response to a fourth excitation current applied via electrodes applied to the right arm and to the left arm; and
- The electrical impedance between the pairs of electrodes is computed utilizing the measured voltages by the at least six measurements according to the electrical model.

Optionally, the at least four electrodes applied to the upper and lower limbs are be applied to the extremities of the limbs, and the at least four electrodes applied to the trunk may be applied to the upper and lower parts of left and right sides of the chest.

The invention may further include utilizing an additional electrode applied to the upper head section for measuring peripheral blood flow parameters utilizing a bipolar electrode configuration. Alternatively, an additional electrode is applied to the upper head section instead of the electrodes applied to the upper limbs, of the measured body.

The invention may also include utilizing an additional electrode applied to the upper head section in the vicinity of the electrode for measuring peripheral blood flow parameters utilizing a tetrapolar electrode configuration. Moreover, at least four additional electrodes may be applied to one of the upper or lower limbs and placed in the vicinity of an excitation electrode, for measuring peripheral blood flow parameters utilizing a tetrapolar electrode configuration.

According to one preferred embodiment of the invention only the active component of the impedance is computed.

In another preferred embodiment of the invention the electrical impedances associated with the aortic flow, pulmonary arterial flow, and pulmonary flow parameters, are obtained by carrying out the following measurements:

measuring the voltage obtained via a right pair of electrodes applied to the upper and lower parts of the right side of the trunk, U1, and the voltage obtained via a left pair of electrodes applied to the upper and lower parts of the left side of the trunk, U12, in response to an excitation current Is applied through electrodes applied to the left arm and to the left leg;

measuring the voltage obtained via a left pair of electrodes applied to the upper and lower parts of the left trunk, U2, and the voltage obtained via a right pair of electrodes applied to the upper and lower parts of the right trunk, U21, in response to an excitation current applied through electrodes applied to the right arm and to the right leg;

measuring the voltage obtained by an upper pair of electrodes applied to the right and left parts of the upper trunk, U3, and by a lower pair of electrodes applied to the right and left parts of the lower trunk, U34, in response to an excitation current applied through electrodes applied to the right leg and to the left leg, and computing the impedance signals:

$$R1 = (U1*U2 - U12*U21)/(Is*(U2-U12))$$ between the right pair of sensing electrodes, $$R2 = (U1*U2 - U12*U21)/(Is*(U1-U21))$$ between the left pair of sensing electrodes, $$R3 = U3*(R1+R2)/(Is*(R1+R2) - U3+U34))$$ between the upper pair of sensing electrodes, and $$R4 = (U34*(R1+R2))/(U3-U34)$$ between the lower pair of sensing electrodes.

The invention may further comprise measuring electrical impedances associated with parameters of the peripheral blood flow by obtaining the electrical impedance associated with the right arm by measuring the voltage obtained via an electrode applied to the arm and an electrode applied to the upper part of the right side of the trunk, where the voltage is being responsive to an excitation current applied via the electrodes; obtaining the electrical impedance associated with blood flow parameters of the left arm by measuring the voltage obtained via an electrode applied to the arm and an electrode applied to the upper part of the left side of the trunk, where the voltage is being responsive to an excitation current applied via the electrodes; obtaining the electrical impedance associated with blood flow parameters of the right leg by measuring the voltage obtained via an electrode applied to the leg and an electrode applied to the lower part of the right side of the trunk, where the voltage is being responsive to an excitation current applied via the electrodes; and obtaining the electrical impedance associated with flow parameters of the left leg by measuring the voltage obtained via an electrode applied to the leg and an electrode applied to the lower part of the left trunk, where the voltage is being responsive to an excitation current applied via the electrodes.

In a further embodiment of the invention an additional pair of electrodes is applied to one of the fingers of the measured body for measuring the electrical impedance associated the parameters of the peripheral blood flow, utilizing a bipolar electrode configuration. An additional pair of electrodes may be also applied to the finger for measuring the electrical impedance associated with parameters of the peripheral blood flow, utilizing a tetrapolar electrode configuration.

The at least six measurements can be performed by selecting a pair of electrodes from the at least four electrodes applied to the upper and lower limbs to be used as excitation electrodes and a pair of electrodes from the at least four electrodes applied to the trunk area to be used as sensing electrodes; continuously generating digital signal corresponding to a sinusoidal signal; converting the digital signal into an analog signal; applying a constant electrical current, the magnitude of which is proportional to the magnitude of the analog signal, via the excitation electrodes; amplifying the voltage over the sensing electrodes; and converting the amplified voltage into a digital signal, which is used for the computation of the impedance signal.

The processing of the amplified voltage converted into a digital signal and the computation of the active component of the impedance and the changes of the component, can include splitting the digital signal into wave-packets, where each wave-packet includes a complete number cycles of the signal; multiplying the wave-packets by a digital sinusoidal waveform with the same frequency and phase as the signal cycles in the wave-packets; summing the results of the multiplication of a wave-packet by the digital sinusoidal waveform; storing the summation results in a memory; calculating the measured resistance by utilizing the summation results and the electrical model; filtering the measured resistance by a low-pass-filter to obtain the mean value of the measured resistance; and subtracting the mean value from the measured resistance to obtain the changes of the measured resistance and basal resistance.

The multiplication of the wave-packet may optionally comprise multiplying each wave-packets signal by itself, thereby raising it to second power, to obtain the impedance value and it changes.

The processing may further include filtering the analog signal by a low-pass-filter, and/or filtering the amplified signal by a high-pass-filter.

The invention may further include utilizing means for measuring ECG signals via at least three electrodes. The electrical current can be an alternating electrical current, and it is preferably produced by a high stability current source.

In the preferred embodiment of the invention the impedance measurements are used for accurately assessing pulmonary systematic and peripheral blood flow and calculating hemodynamic parameters of the probed sections. The resistance R for assessment of peripheral blood flow parameters is preferably computed utilizing the excitation current Is and the measured voltage Ua, as follows: R=Ua/Is.

According to one preferred embodiment of the invention the sample rate of the voltage measurements and of the ECG signal is at least 200 sample/sec.

BRIEF DESCRIPTION OF THE DRAWINGS

In the drawings:

FIGS. 2A-2I illustrates various measurements obtained utilizing the electrodes arrangement shown in FIG. 1;

FIGS. 4A-4E illustrates measurements obtained utilizing the electrodes arrangement shown in FIG. 3A;

DETAILED DESCRIPTION OF PREFERRED EMBODIMENTS

The present invention provides a noninvasive method and apparatus for the monitoring of hemodynamic parameters in different parts of the human body simultaneously, based on measurements of electrical impedances. The invention provides an improved measurement scheme which is based on a unique electrode arrangement and an innovative electrical model, which are combined to obtain accurate impedance measurements of distinct body sections by considering the excitation current distortion components which are due to electrical currents flowing in the section of the measured body which are not subjected to the actual measurement. In this way the accuracy of the measured basal impedance Z (basal resistance R) and $\Delta Z$ ($\Delta R$) is substantially increased, and consequently the accuracy of the calculations of the hemodynamic parameters is also substantially increased.

In the present invention, the source electrodes are situated on the distal extremities of the measured body. This is similar to the measurement performed in standard whole body impedance measurement, but it is different in that the detector electrodes are situated on the trunk. Using this electrode array substantially minimizes the cyclical changes, and it also provides for the retrieval of stable values throughout the respiratory cycle. In addition, by having the source electrodes situated on the distal limbs and the detector electrodes on the anterior chest, the changes in the measured impedance that are due to the changes in the lung volume are substantially reduced. The impedance measurements are further improved by considering the excitation current distortion components resulting from electrical currents flowing in the sections of the measured body which are not subjected to the actual measurement.

Figure 1:
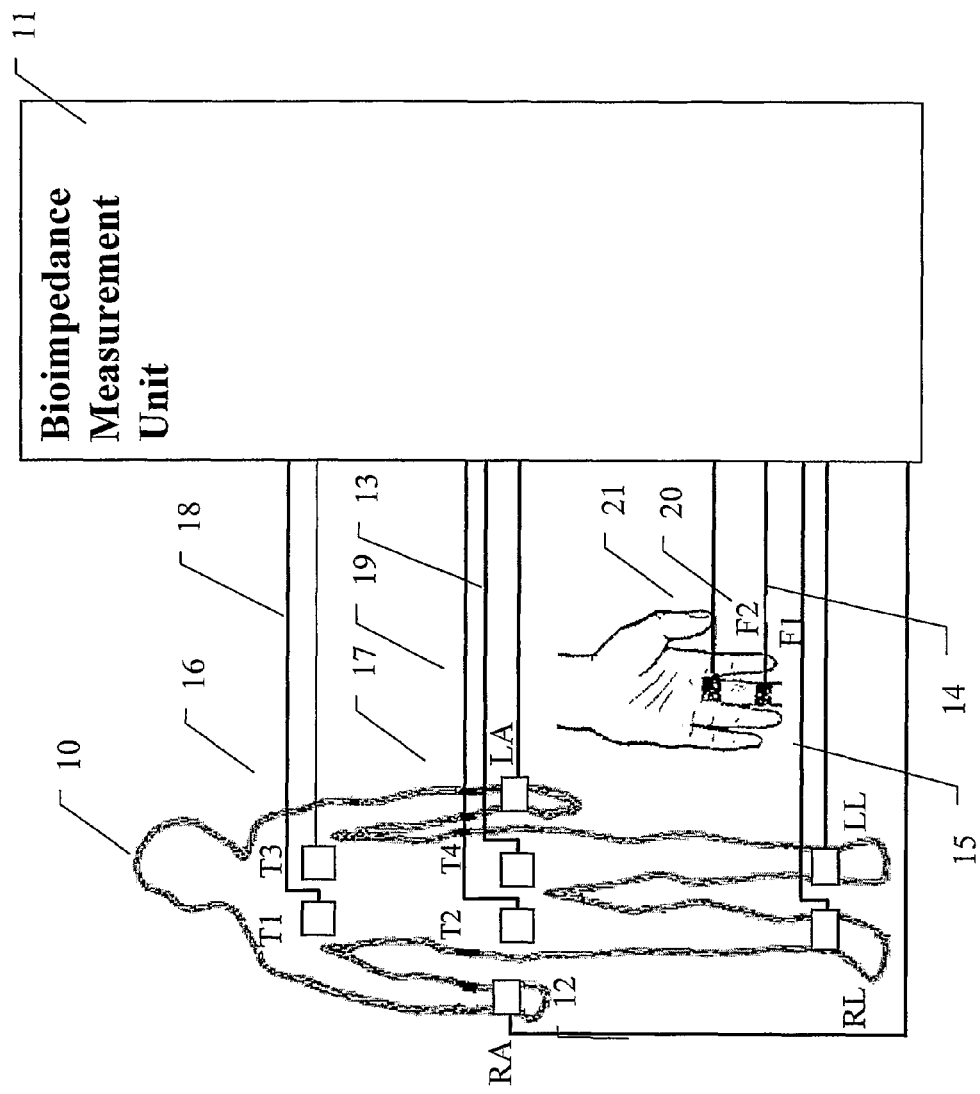
FIG. 1 illustrates a measurement arrangement according to a preferred embodiment of the invention.

FIG. 1 illustrates an electrode arrangement for use with the apparatus of the invention for noninvasive determination of pulmonary, systematic and peripheral blood flow hemodynamic parameters. The apparatus comprises an electrical impedance measurement unit 11 and an electrode arrangement consisting, for example, of ten electrodes.

In the example of FIG. 1 four excitation electrodes 12-15 are situated on the distal ends of the limbs of the measured body 10. The excitation electrodes 12-15 of the arrangement are applied to the distal part of the right arm (12), to the distal part of the left arm (13), to the distal part of the right leg (14), and to the distal part of the left leg (15). These excitation electrodes 12-15 are preferably of a stripe electrode type. In this example, four sensing electrodes 16-19 of the arrangement are situated as follows: electrode 16 is applied to the upper part of the right trunk (T1); electrode 17 is applied to the lower part of the right trunk (T2); electrode 18 is applied to the upper part of the left trunk (T3); and electrode 19 is applied to the lower part of the left trunk (T4). The sensing electrodes 16-19 are preferably a type of spot electrode. An additional pair of electrodes 20-21 are situated on the patient finger as follows: electrode 20 of the arrangement is applied to the upper part of finger (F1); an electrode 21 is applied to the lower part of finger (F2). The electrodes 20 and 21 are preferably of a stripe electrode type. The electrical impedance measurement unit 11 uses electrodes 12-15 for picking up ECG and electrical impedance signals.

In a preferred embodiment of the invention the electrical impedance measurement unit 11 realizes 8-channels of measurement of electrical impedances, with time separation between channels, and measurement of ECG signals. The unit 11 is preferably capable of measuring the following parameters:

parameters of peripheral blood flows in the extremities and the arm finger of the patient; and parameters of central blood flows of the patient such as parameters of pulmonary arterial, pulmonary, and aortic blood flows.

The measurement unit 11 calculates the hemodynamic parameters of the patient and indicates the parameters, ECG trace, and eight waveforms of resistance changes obtained from each of the electrical impedance measurement channels.

Figure 6:
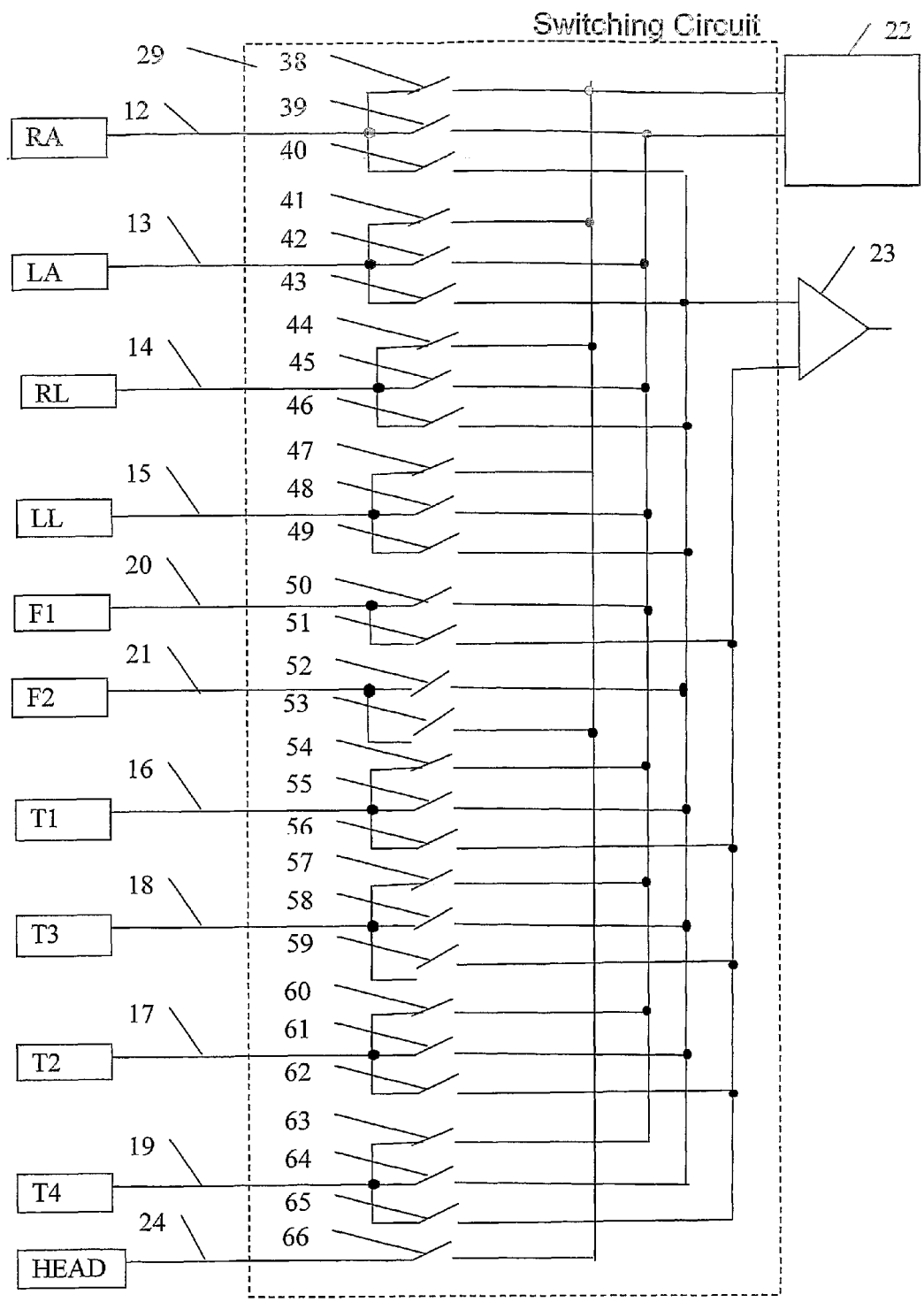
FIG. 6 is a block-diagram illustrating a preferred embodiment of the switching circuit.

In order to measure parameters of the patient's central blood flows, the measurement unit 11 uses a tetrapolar system of electrodes. Various measurement configurations, utilizing the electrode arrangement of the invention, for determining the parameters of the central blood flows of the patient, are shown in FIGS. 2A-2C. In the tetrapolar system of electrodes, the current source 22 is used for injecting an alternating current through two current electrodes into the patient body 10. Amplifier 23 is used for picking up the voltage signal obtained from the two pairs of sensing (potential) electrodes placed onto different segments of the trunk. The two pairs of electrodes (excitation and sensing) that are used for each measurement are switched in turn, as will be explained in details (FIG. 6).

The current source 22 and the amplifier 23 are preferably placed in the electrical impedance measurement unit 11 and their operation will be explained herein below during the description of operation of the unit 11. Throughout the following discussion the configurations will be also referred to as Electrical Impedance Leads (EBI) or EBI Leads. During the measurement of the parameters of the central blood flows, the unit 11 uses the following three EBI leads:

EBI Lead 1 to measure aortic flow parameters (FIG. 2A);

EBI Lead 2 to measure pulmonary arterial flow parameters (FIG. 2B); and

EBI Lead 3 to measure pulmonary flow parameters (FIG. 2C).

Figure 2I:
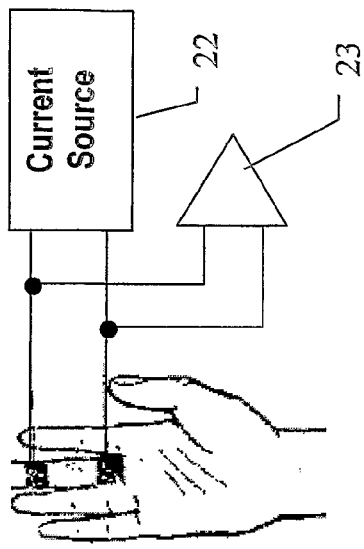
Figure 2H:
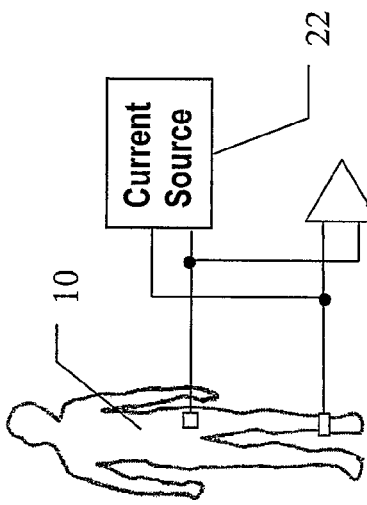
Figure 2G:
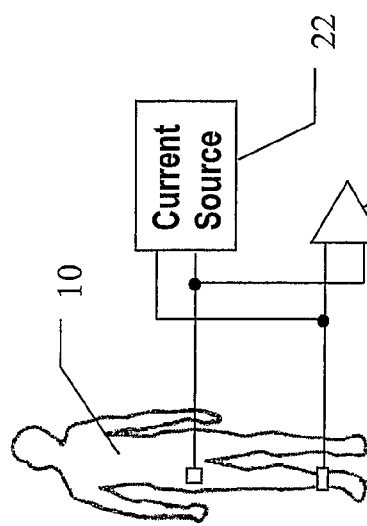

For the purpose of measuring parameters of the peripheral blood flow in the extremities and the arm finger of the patient, the unit 11 optionally uses a pair of electrodes of a bipolar system (FIG. 2I). In the bipolar system, a current source 22 injects alternating current into the patient body 10 through two electrodes, and the amplifier 23 picks up the voltage signal obtained from the same electrodes, i.e., the same electrodes are used for excitation and for sensing.

Different measurement configurations, utilizing the electrode arrangement of the invention, can be employed to determine parameters of the peripheral blood flow in the extremities, in the arms, legs, and finger of the patient, as shown in FIGS. 2E-2I. In order to measure the parameters of the peripheral blood flows, the electrical impedance measurement unit 11 uses the following five EBI Leads: LA for the left arm (FIG. 2F); RA for the right arm (FIG. 2E); RL for the right leg (FIG. 2G), LL for the left leg (FIG. 2H); and F for the finger (FIG. 2I)

Figure 3A:
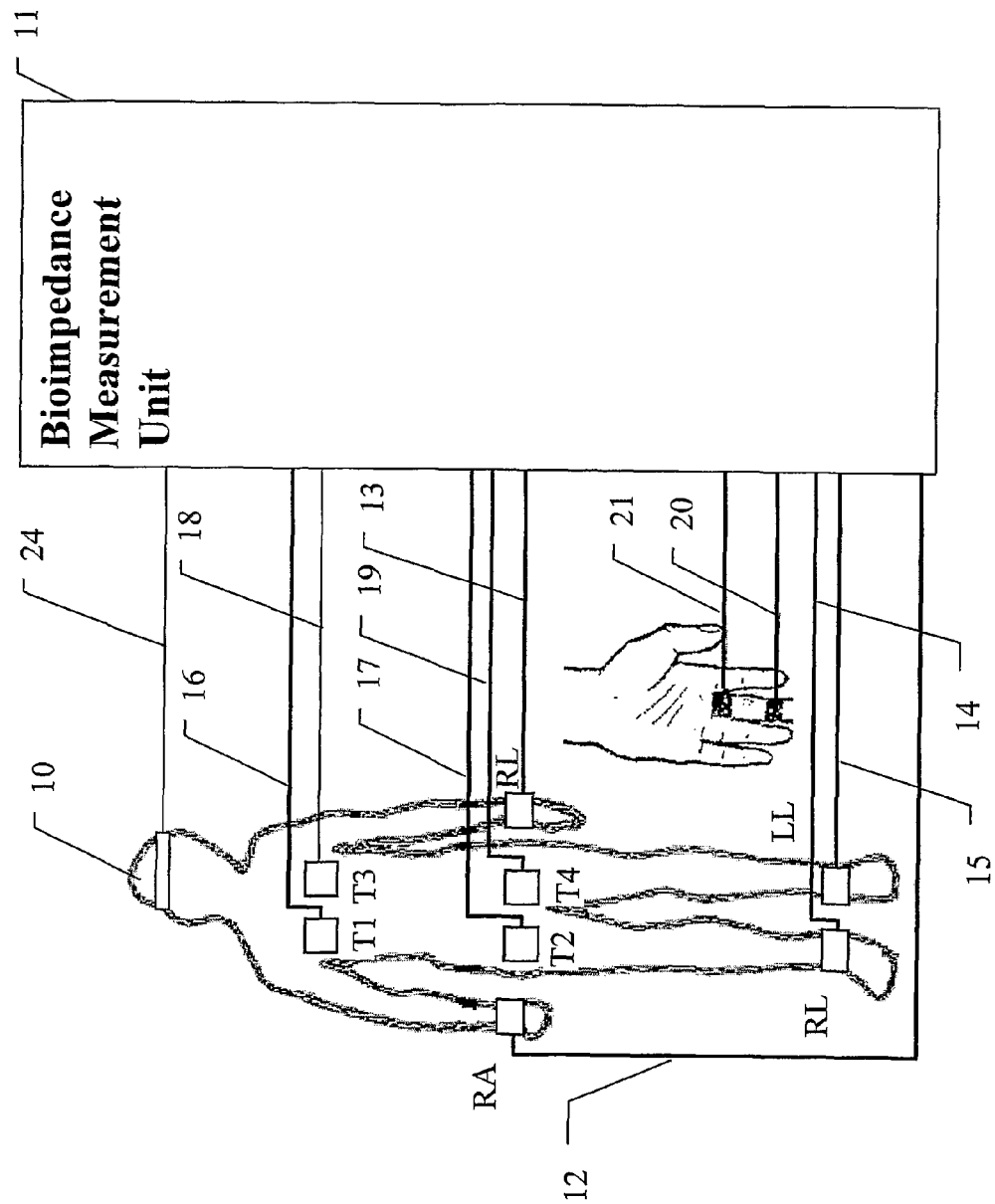
FIG. 3A illustrates an electrode arrangement, in which an additional electrode is applied to the patient's head, according to another preferred embodiment of the present invention.
Figure 3B:
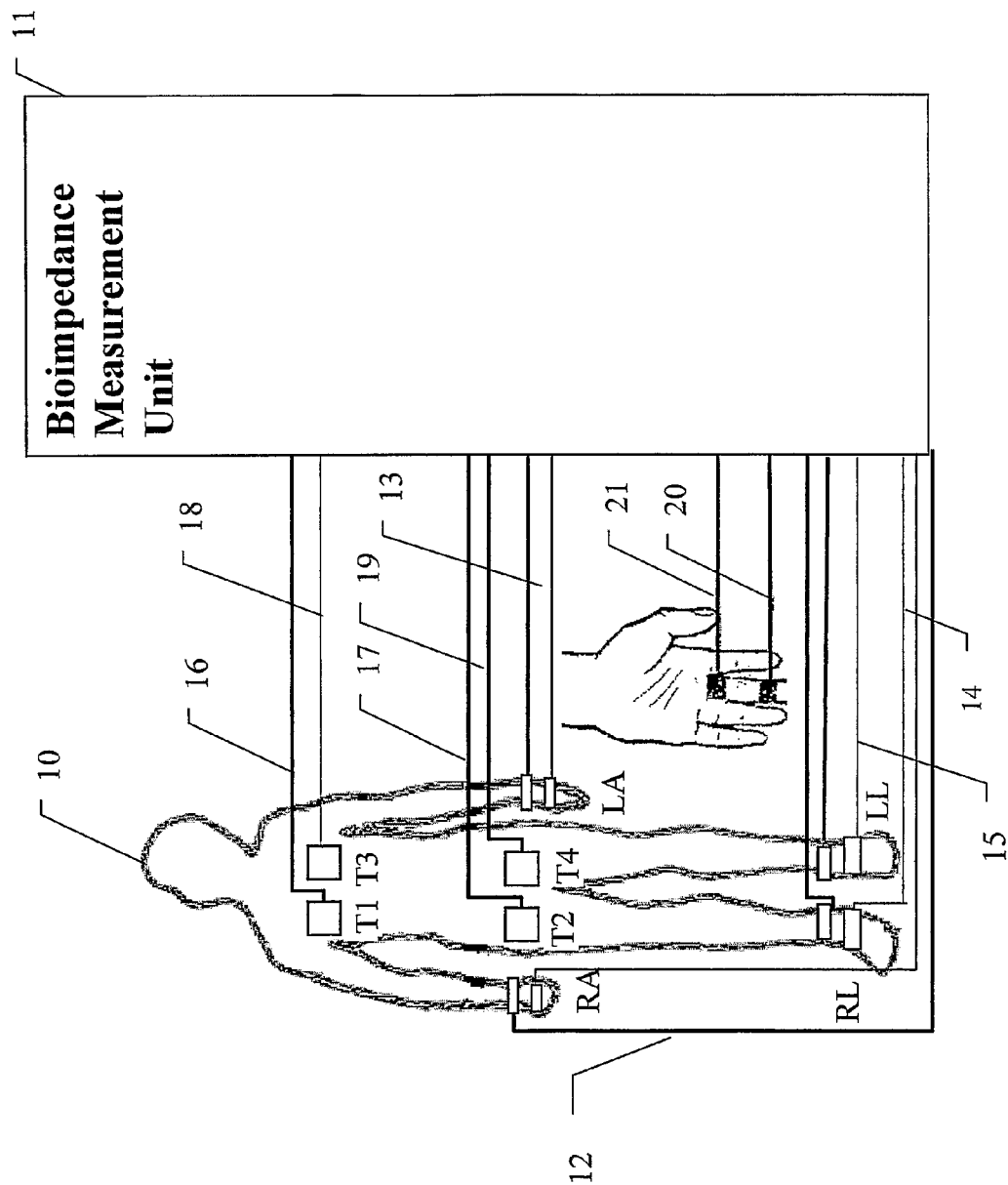
FIG. 3B illustrates another electrode arrangement, in which an additional electrode is applied to the patient's extremities utilizing a tetrapolar electrode configuration, according to yet another preferred embodiment of the present invention.

It should be understood that the measurements of the peripheral blood parameters are preferably carried out utilizing a tetrapolar measurement for all peripheral leads including finger channel, as exemplified in FIG. 3b. Although in the preferred embodiment of the invention bipolar measurements are utilized for the measurements of the peripheral blood parameters, the description of the embodiments is sufficient to achieve the same measurements utilizing tetrapolar measurements. While variations may be required for this purpose, persons skilled in the art are fully capable of determining them.

If the medical conditions of the patient, such as tremor, do not allow obtaining a reliable signal from the arms, then an additional stripe electrode 24 can be applied to the patient's head as shown in FIG. 3A. Different configurations of electrodes are employed for the different EBI Leads measurements, as shown in FIGS. 4A-4E.

Figure 3C:
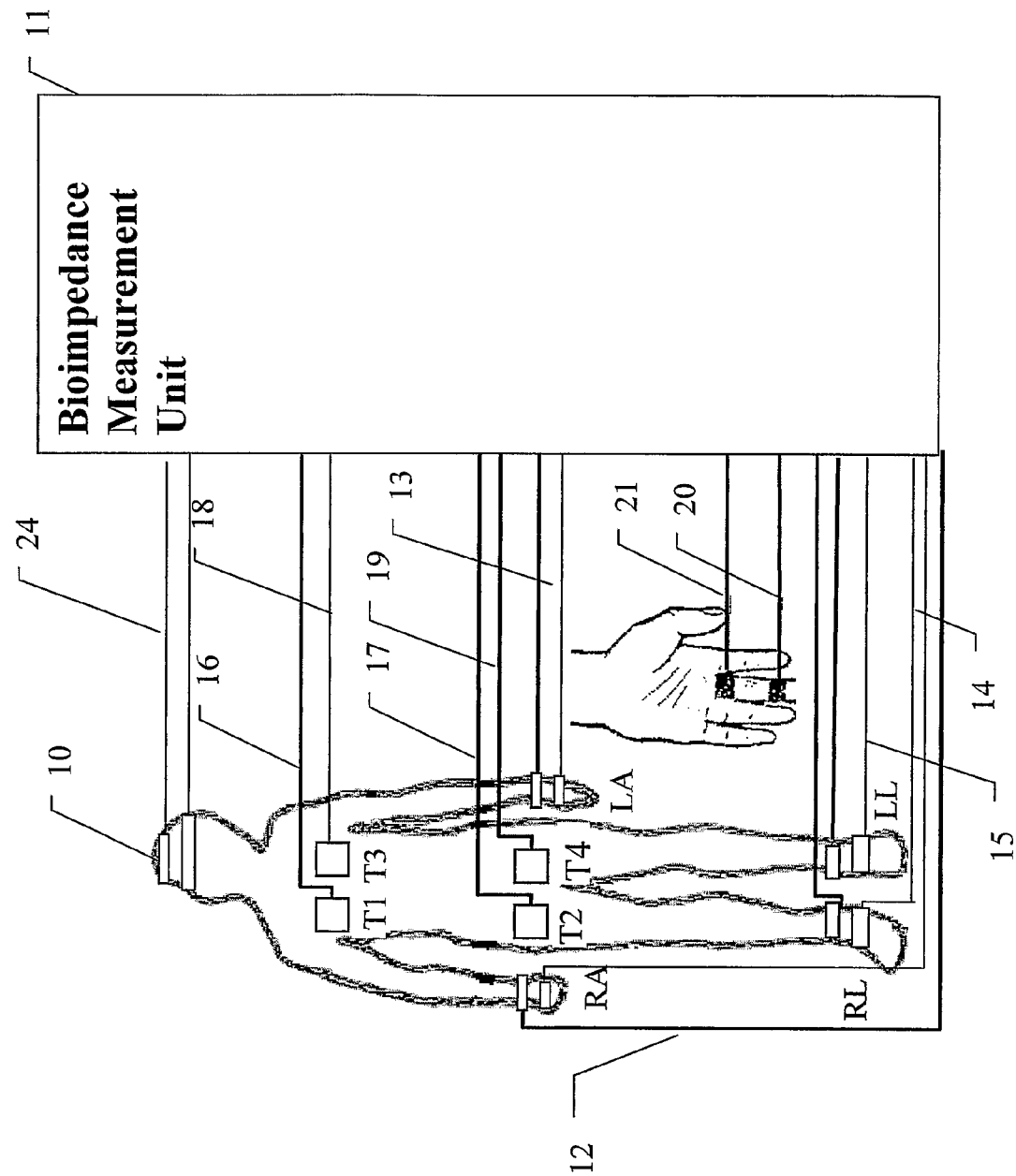
FIG. 3C illustrates a further electrode arrangement, in which an additional electrode is applied to the patient's head and extremities utilizing a tetrapolar electrode configuration, according to an additional embodiment of the present invention.
Figure 5:
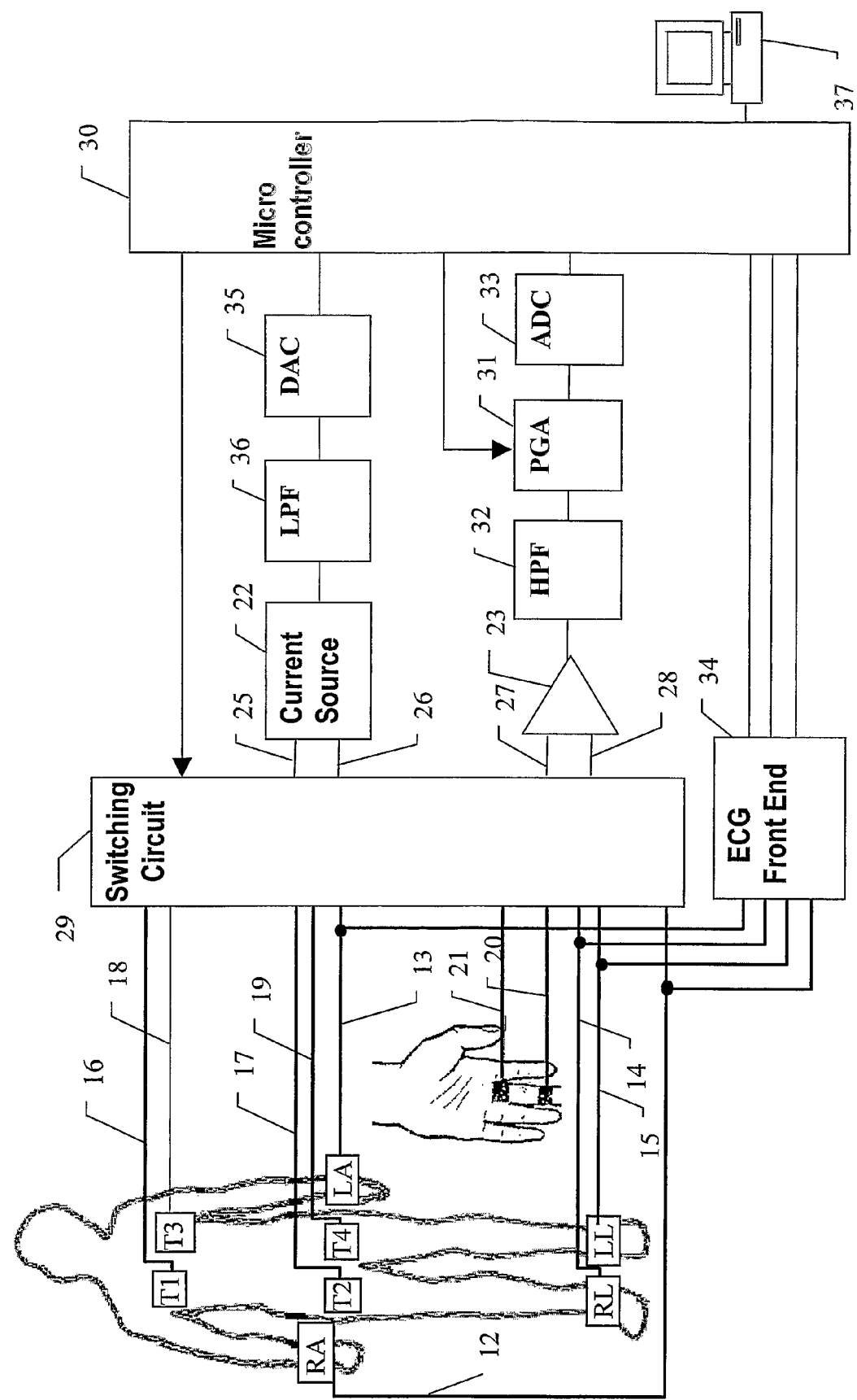
FIG. 5 is a block diagram illustrating the electrical impedance measurement unit.

It should be noted that applications of the apparatus according to the present invention are not limited by measurement of electrical impedance signals of the patient's body sections shown in FIGS. 3 and 5, but can also include measurement of electrical impedance signals of other sections of the body as well. As discussed hereinabove, both bipolar and tetrapolar configurations can be used for each section. In addition, as will be demonstrated hereinafter, each electrode can function both as a sensing and excitation electrode, so that the actual functioning of each electrode in each measurement, according to the invention, is eventually effected by utilizing switching means.

FIG. 5 is a block diagram illustrating the electrical impedance measurement unit 11. The electrodes 12-21 are coupled to the terminals 25 and 26 of the current source 22, and to the inputs 27 and 28 of the instrumental amplifier 23 through a switching circuit 29. The switching circuit 29 provides the required connectivity between electrodes 12-21 and the terminals 25 and 26 of the current source 22 and to the inputs 27 and 28 of the instrumental amplifier 23, according to an activation process, which will be described in detail herein below. The microcontroller 30 provides the required control and processing for timing of the switching circuit 29, and for measuring both the ECG signals and the electrical voltages and computing the impedance and its changes within 5 msec, in a sample rate of at least 200 sample/sec.

The microcontroller 30 utilizes a look-up table of digital values of the amplitudes of a sine wave, which are preferably stored in a ROM (Read Only Memory) device. During the measurement, the stored digital values are continuously fed into a Digital to Analog Converter (DAC) 35. The Low Pass Filter (LPF) 36 is used to provide a smooth analog sine signal from the converted signal provided by the DAC 35. The smoothed sine signal drives the input of the voltage-controlled current source 22. The current source 22 injects a stable alternating current, for example, of 50 kHz and 2.0 mA RMS through the excitation electrodes into the patient body 10. For each measurement a pair of electrodes from the set of electrodes 12-15 is selected as excitation electrodes according to the state of the switching circuit 29.

The instrumental amplifier 23 picks up signals from the potential (sensing) electrodes and excitation electrodes that are obtained via the switching circuit 29. The excitation electrodes 16-19 can also function as sensing (potential) electrodes, according to the state of the switching circuit 29.

The measured signals obtained from the output of the amplifier 23 are passed through a High Pass Filter (HPF) 32 to the software Programmable Gain Amplifier (PGA) 31, the output of which is fed to the input of a high frequency Analog to Digital Converter (ADC) 33. The HPF 32 is preferably a Butterworth filter of the second order operating with a cutoff frequency which equal to or slightly smaller than the frequency of the excitation current. The HPF filter 32 is used to remove noise interferences, particularly in 50 or 60 Hz frequencies, which induce measurement interferences. The microcontroller 30 sets the operating gain of the PGA 31, the value of which depends on the level of the electrical signal obtained at the input terminals of the amplifier 23. The microcontroller 30 receives the digitalized electrical signal data retrieved from the output of the ADC 33, which are then used for further digital processing.

The four-electrode ECG front-end 34 picks up ECG signals from the excitation electrodes 12-15. The ECG front-end 34 derives up to six basic ECG leads (I, II, III, AVR, AVL, and AVF) and transfers up to six ECG signals to the analog front-end (not shown) embedded in the microcontroller 30. The ECG analog signals are received by the controller 30 and used for carrying out digital processing of the ECG signals. The microcontroller 30 conveys the results of the measurements to the computer system 37, which can be a personal computer, a notebook, a hand-held device, a mainframe, or the like. The computer system 37 carries out the following functions: realization of a user interface; calculation of hemodynamic parameters; control of the microcontroller 30; and management of a database of analysis results and patients' information.

The microcontroller 30 can be implemented utilizing a 16-bit digital signal controller, e.g., dsPIC 30F 6011 manufactured by Microchip Technology, Inc. The microcontroller 30 preferably combines functions of the 16 analog inputs and 12-bit resolution ADC converter, and a microprocessor with capabilities of a digital signal processor (DSP).

One of the most challenging problems facing electrical impedance methods of research of the blood flow in the human body is the accuracy of the measurement of the impedance Z and of the impedance change $\Delta Z$ required for the assessment of the hemodynamic parameters. An active component of impedance R, and the changes of resistance $\Delta R$, can be used instead of Z and $\Delta Z$ for determination of the hemodynamic parameters. The apparatus according to the present invention uses the values of R and $\Delta R$ to determine the hemodynamic parameters, and in this case the influence of the reactive components of the impedance on the obtained hemodynamic parameters values is excluded, which increases the accuracy of the blood flow measurements.

In the following a method for measuring the values of R and $\Delta R$ for four segments of the human trunk will be discussed. As will be understood by those skilled in the art, this method can be realized utilizing different numbers of segments and can be applied to other parts of the human body.

The distortions of the excitation currents discussed hereinbefore, result in large errors, which introduce distortions in the measurements of R and $\Delta R$ in the human body. These errors are especially serious when the electrical impedance measurements are carried out on the ill, wherein the results of the measurements are usually not reliable. A method for the accurate measurement of R in segments of the patient's body wherein the accuracy of the measurement does not depend on the value of the distortion will be described hereinafter.

Figure 7:
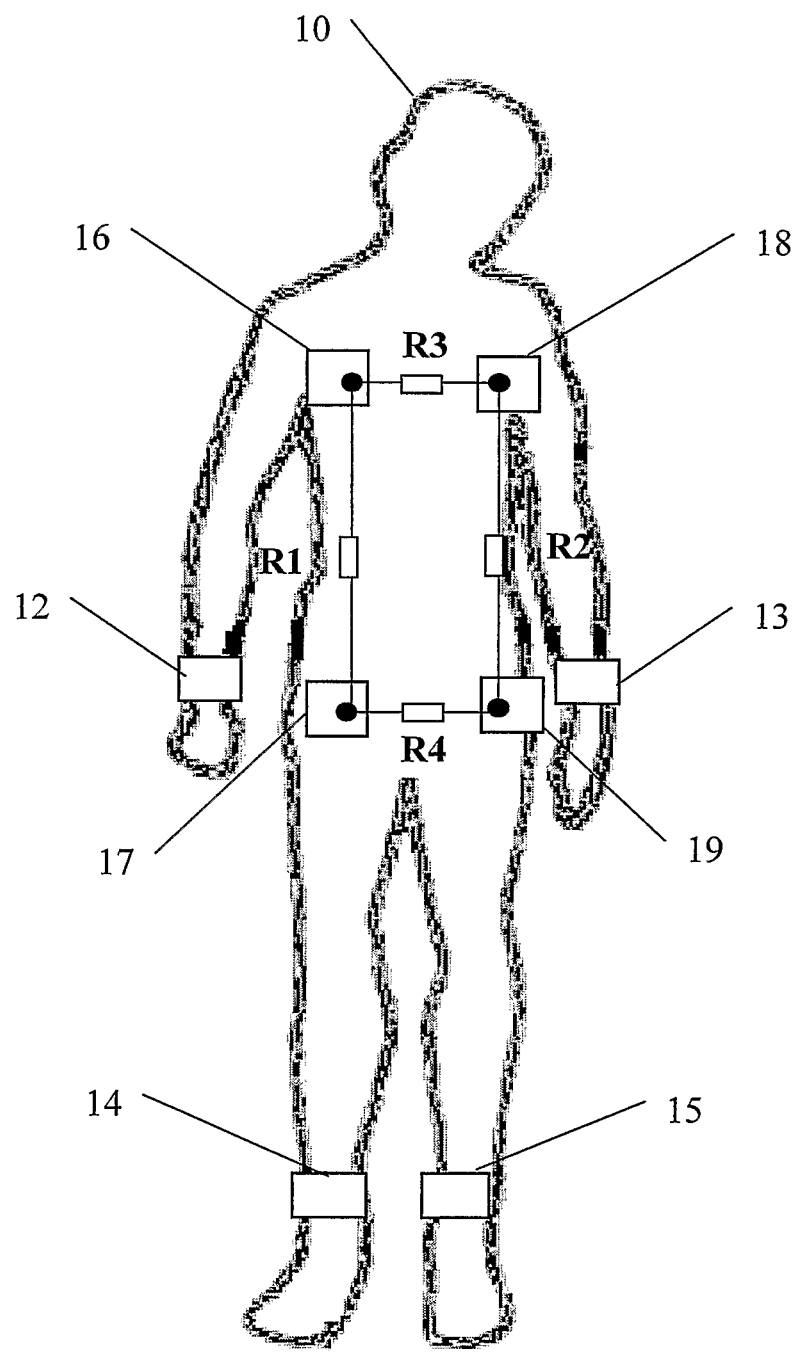
FIG. 7 shows an electrical model of an impedance circuit of the trunk, according to a preferred embodiment of the invention.
Figure 8B:
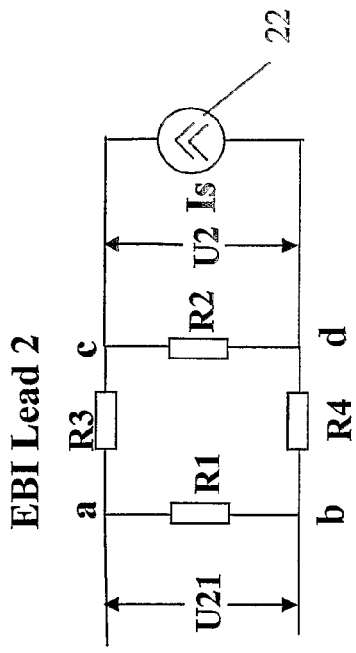
FIGS. 8A-8C are block-diagrams illustrating voltage measurements obtained utilizing the model shown in FIG. 7.
Figure 8C:
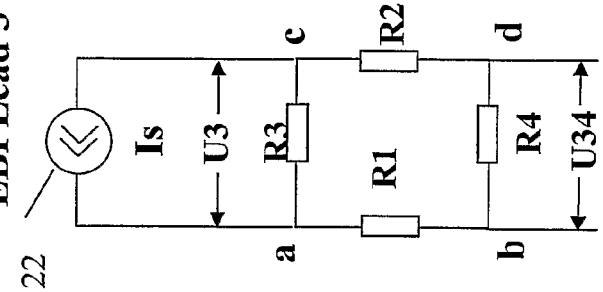
Figure 8A:
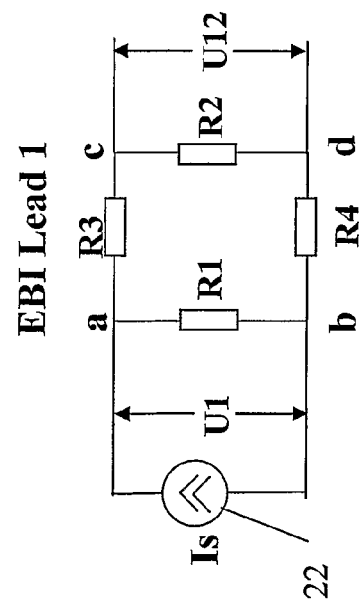

According to the present invention, the apparatus carries out multi-channel measurement of the resistance in four leads of the human trunk: EBI lead 1, EBI lead 2, EBI lead 3, EBI lead 4, as shown in FIGS. 2A-2D. FIG. 7 shows an electrode arrangement applied to the patient trunk according to a preferred embodiment of the invention. The resistances between pairs of electrodes applied to the patient trunk represent an equivalent circuit consisting of four resistors R1-R4. FIGS. 8A-8C show the distribution of the voltages in the equivalent circuit for the different EBI leads measurements.

The electrical model of the invention should be modified if the measurements of the central blood flows are carried out utilizing an electrode applied to the patient's head as shown in FIGS. 3, and 3A-B. In this case the R3 resistor (FIG. 7) should become an electrical "short circuit", namely, the electrical model is modified to include only the R1, R2, and R4 resistors as illustrated in FIG. 7, but without the R3 resistor, which is electrically "shortened", so that resistor R1 is connected directly to R2. As will be appreciated by those skilled in the art, the measurement of the same central blood flows can be obtained utilizing this configuration, as in the other embodiments of the invention.

FIG. 8A shows an equivalent circuit for the measurement of voltages in the EBI lead 1 (FIG. 2A). The excitation current Is from the Current Source 22 is applied to nodes a and b of the equivalent circuit via excitation electrodes 12 and 14, and the resulting voltages, voltage U1, between nodes a and b, and the voltage U12, between nodes c and d, are measured via the pairs of sensing electrodes (16, 17) and (18, 19) respectively.

FIG. 8B shows an equivalent circuit for the measurement of the voltages in the EBI lead 2 (FIG. 2B). The excitation current is applied to nodes c and d of the equivalent circuit via excitation electrodes 13 and 15 and the resulting voltages, voltage U2, between nodes c and d, and voltage U21, between nodes a and b, are measured via the sensing electrode pairs (16, 17) and (18, 19) respectively.

FIG. 8C shows an equivalent circuit for the measurement of the voltages in the EBI lead 3 (FIG. 2C). The excitation current (Is) is applied to nodes a and c of the equivalent circuit and the voltage U3, between nodes a and c, and the voltage U34, between nodes b and d, are measured via the sensing electrode pairs (16, 18) and (17, 19) respectively.

The apparatus calculates the resistances of the segments of the patient's body using the values of the measured voltages utilizing the following equations:

$$R1 = (U1 * U2 - U12 * U21) / (Is * (U2 - U12)) \qquad (1)$$

$$R2 = (U1 * U2 - U12 * U21) / (Is * (U1 - U21)) \qquad (2)$$

$$R3 = U3 * (R1 + R2) / (Is * (R1 + R2) - U3 + U34)) \qquad (3)$$

$$R4 = (U34 * (R1 + R2)) / (U3 - U34) \qquad (4)$$

The operation of the switching circuit 29 is explained in the block diagram shown in FIG. 6. The switching circuit 29 preferably contains 29 switches 38-66. The switches' ON state designates that the required connection is established to let the signals pass between the electrodes 12-21, 24, the current source 22, and the amplifier 23. The state of the switches in each one of the EBI leads is shown in Table 1.

TABLE 1

| Selected EBI Lead | Switches in ON state |
|---|---|
| EBI Lead 1.U1 measurement | 38, 45, 55, 62 |
| EBI Lead 1.U12 measurement | 38, 45, 58, 65 |
| EBI Lead 2.U2 measurement | 41, 48, 58, 65 |
| EBI Lead 21.U21 measurement | 41, 48, 55, 62 |
| EBI Lead 3.U3 measurement | 38, 42, 55, 59 |
| EBI Lead 3.U34 measurement | 38, 42, 61, 65 |
| EBI Lead RA | 38, 40, 54, 56 |
| EBI Lead LA | 41, 43, 57, 59 |
| EBI Lead RL | 44, 46, 60, 62 |
| EBI Lead LL | 47, 49, 63, 65 |
| EBI Lead F | 50, 51, 52, 53 |
| EBI Lead 1 for the electrode arrangement with the head electrode.U1 measurement | 66, 45, 55, 62 |
| EBI Lead 1 for the electrode arrangement with the head electrode.U12 measurement | 66, 45, 58, 65 |
| EBI Lead 2 for the electrode arrangement with the head electrode U2 measurement | 66, 48, 58, 65 |
| EBI Lead 2 for the electrode arrangement with the head electrode U21 measurement | 66, 48, 55, 62 |

The set of switches 38-66 of the switching circuit 29 depicted in FIG. 6 provides for the configuration of the electrodes for each of the EBI leads shown in FIGS. 2A-2I and FIGS. 4A-4E. It is obvious that other methods of multi-channel electrical impedance measurements in other sections of the patient's body can be realized using the same or another configuration of the switches.

Another goal of the present invention is reduction of noise distorting the electrical impedance measurement. Reduction of the distorting noise is an important goal, since during the electrical impedance measurements; very small changes of impedance $\Delta Z$ (about tenths of Ohm, $\sim 1/10 \, \Omega$) must be measured while the values of the measured base impedance is about 100 Ohms. Thus, the level of the noise component in the measured signal must not exceed 0.001 Ohm in order to obtain acceptable measurement results. The removal of noise in a multi-channel apparatus is a complicated task, because in such apparatus the measurement time available for each channel decreases in a proportional ratio with the number of channels.

Usually, an analog rectifier is used to obtain Z from the electrical impedance signal, as described, for example, in U.S. Pat. No. 5,529,072. However, the analog rectifier does not allow obtaining an active component R of the measured electrical impedance Z. The use of a synchronous detector can be exploited to obtain the active component and to reduce the noise level. Nevertheless, the measurement of R is preferable over the measurement of Z, since it excludes the influence of capacitance effects of the patient's body on the results of the assessment of the blood flow parameters. Unfortunately, conventional synchronous detectors include a low pass filter at the output stage that increases the bandwidth of the third harmonic up to the cut off frequency of the filter.

The digital signal processing method used in the present invention allows excluding the third, and higher, harmonics which are due to the presence of noise in the input signals. According to this preferred method, the microcontroller 30 is capable of determining both the value of the body resistance R, by multiplying the ADC conversions outputs by the sine waveform generated by the microcontroller 30, and the value of the electrical impedance Z, by raising the ADC outputs to the second power.

Figure 9:
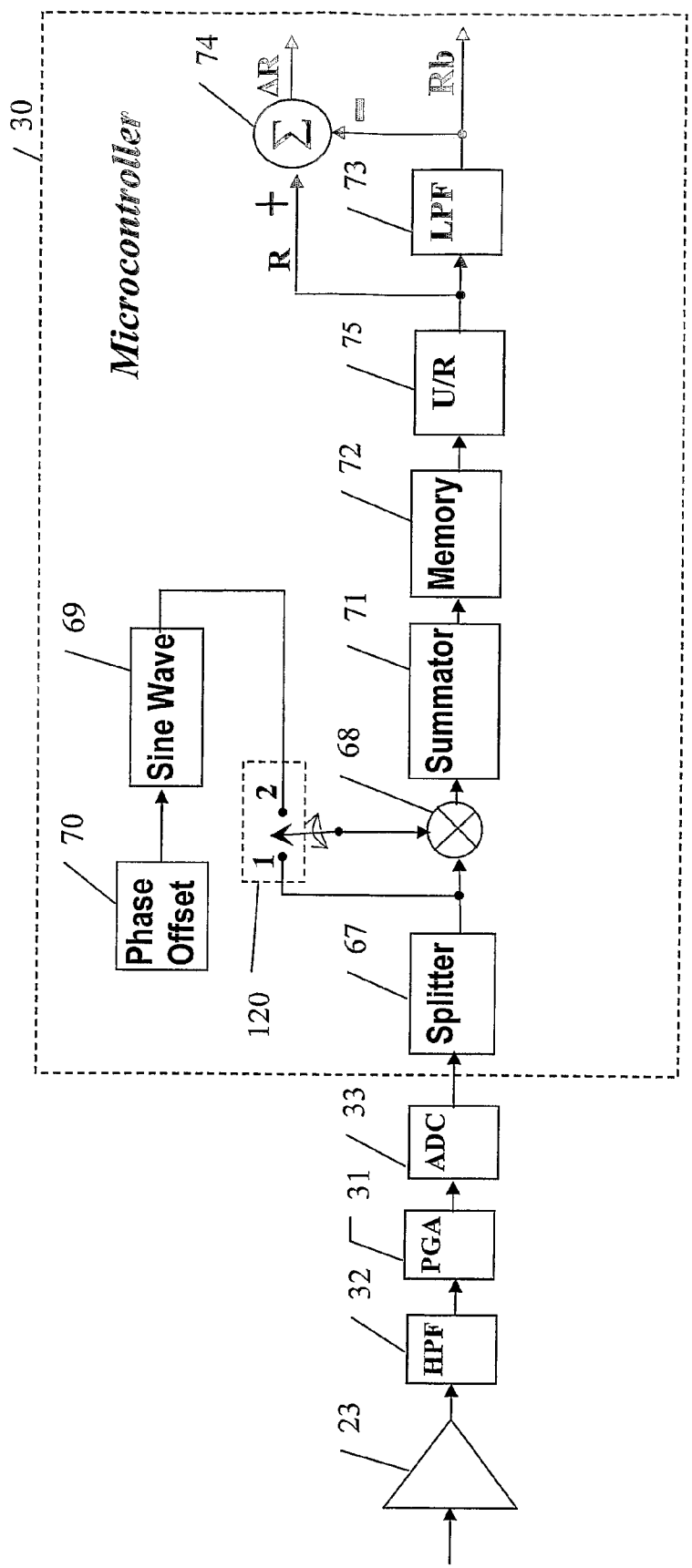
FIG. 9 is a block diagram illustrating a preferred implementation of the electrical impedance waveform processing.

The digital signal processing of the electrical impedance waveform that is carried out by the apparatus of the invention is schematically illustrated in FIG. 9.

Although the apparatus of the present invention is capable of measuring the impedance Z and the active component of the impedance R, only the active component R is needed to determine the blood flow parameters, as will be described herein below. It should be noted that the ability of the apparatus to measure the impedance Z is a useful feature that can be of course used to assess the body composition.

The ADC 33 delivers the digitalized signal to a splitter 67, which outputs wave packets, each of which consists of a sequence of complete cycles (i.e., 0-2π) of the sinusoidal waveforms received from the ADC 33, where the number of complete cycles in each wave packet is set to a predetermined integer number. The microcontroller 30 generates a look-up table produced sine wave 69 analogous to a sine wave generated by the microcontroller 30 for the DAC 35 (see FIG. 5). A block (phase offset) 70 sets the phase shift of the sine wave 69 to a value equal to the phase shift of the signal obtained via the HPF 32, and other analog components.

The wave packets arrive to an input of the multiplier 68. If the active impedance component R should be measured, the sine signal 69 is switched by switch 120 (state 2) into the multiplier's second input, which resultantly generates a multiplication of the two waves. In the case wherein the impedance Z should be measured, the ADC 33 delivers the digitalized signal to the second input of the multiplier 68 by switching switch 120 into state 1, and in this case the multiplier 68 generates a product of the input sine wave raised to the second power.

The summator 71 outputs the summation of the waveforms produced by the multiplier 68. The sum of the amplitudes of each wave packet corresponds to the values of the active component Ua of the measured voltage sensed by the amplifier 23 (when the switch 120 is in state 2). Whenever this process is completed for each wave packet, the summation result is stored in memory 72 and the summator 71 is reset to null. The results of this process are stored in memory 72, which provides the stored results to a conversion unit 75 (U/R). The conversion unit 75 calculates R1-R4 resistance (or impedance if switch 120 is in state 2) values according to equations (1)-(4) for EBI leads 1-4, or alternatively resistances (impedances) of peripheral sections are computed for EBI leads RA, LA, RL, LL, and F, according to equation 5 herein below:

$$R = Ua/Is \quad (5)$$

Is—is the excitation current.

The value of R represents the sum of the value of the basal resistance Rb and the value of the resistance deviation ΔR from the basal resistance.

$$R = Rb + \Delta R$$

The LPF 73 filters a sequence of values of R delivered from the conversion block 75 and provides the value of Rb on its output. The subtractor 74 subtracts Rb from the sequence of values of R delivered from the conversion block 75 and outputs a sequence of values of ΔR.

The signal processing illustrated in FIG. 9 is preferably performed utilizing digital DSP means. However, as will be appreciated by those skilled in the art, the same results can be obtained utilizing equivalent analog means. Of course, in case analog signal processing is utilized, the ADC 33 is not needed.

Figure 10:
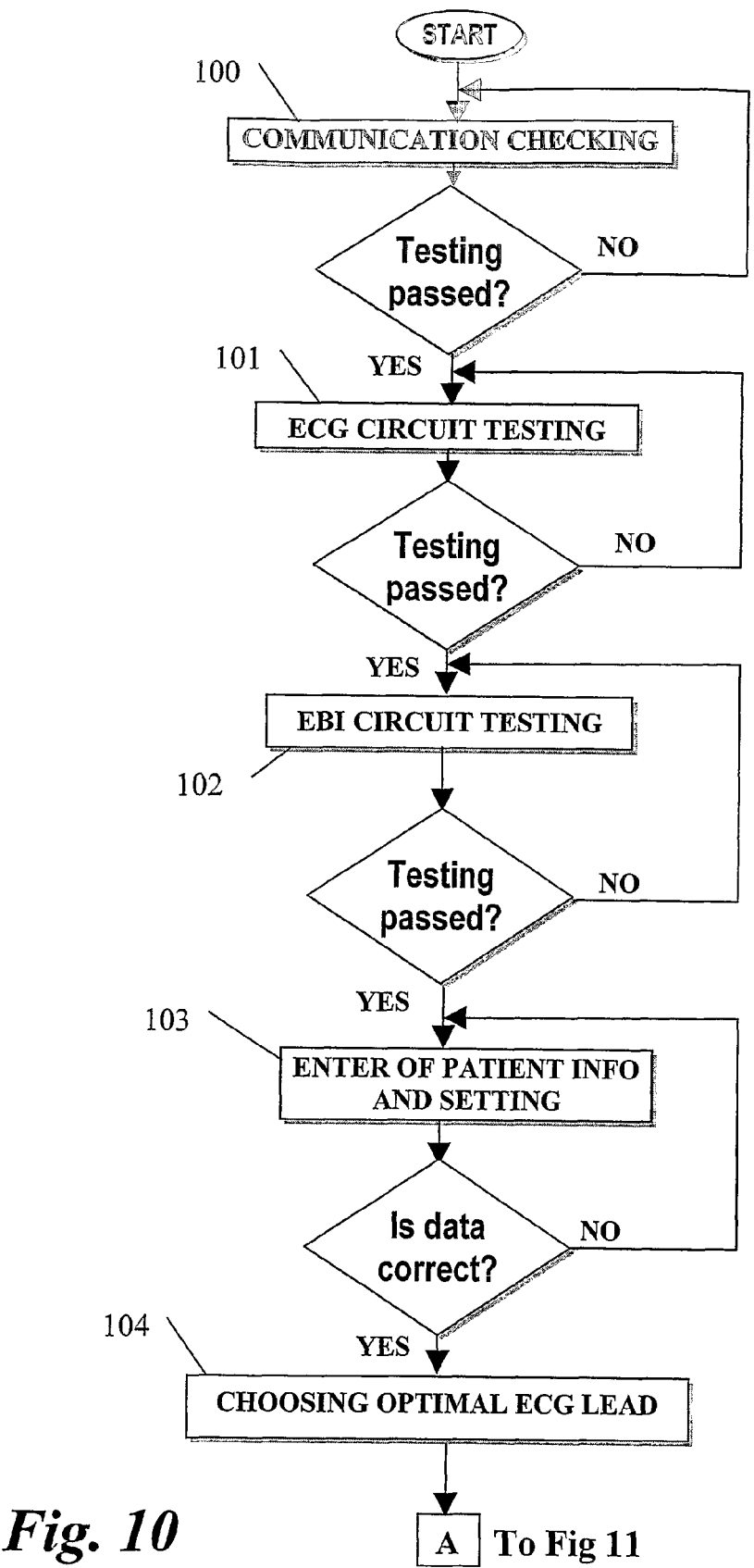
FIGS. 10-12 are flowcharts illustrating a preferred algorithm for performing the apparatus functions.
Figure 11:
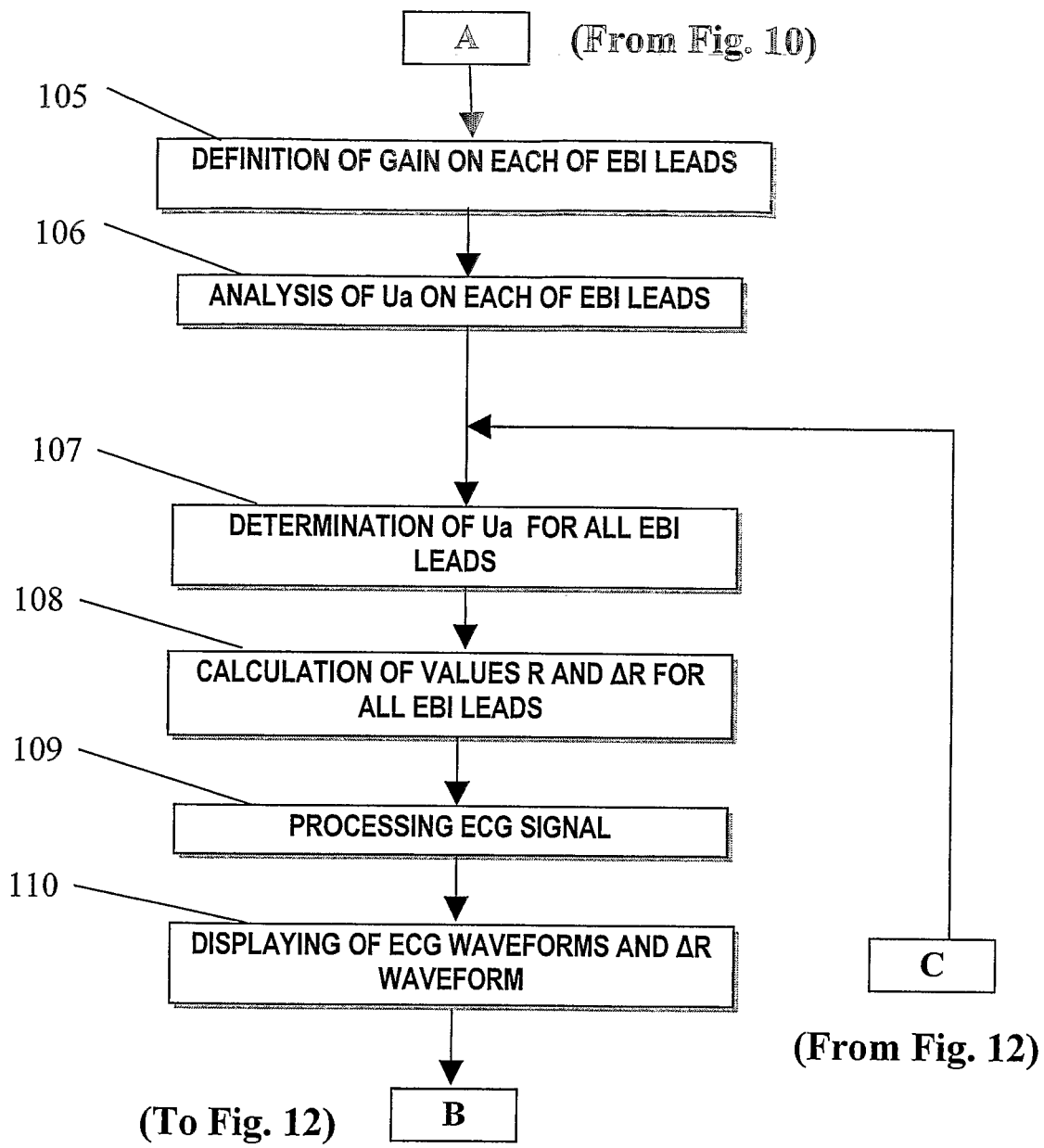
Figure 12:
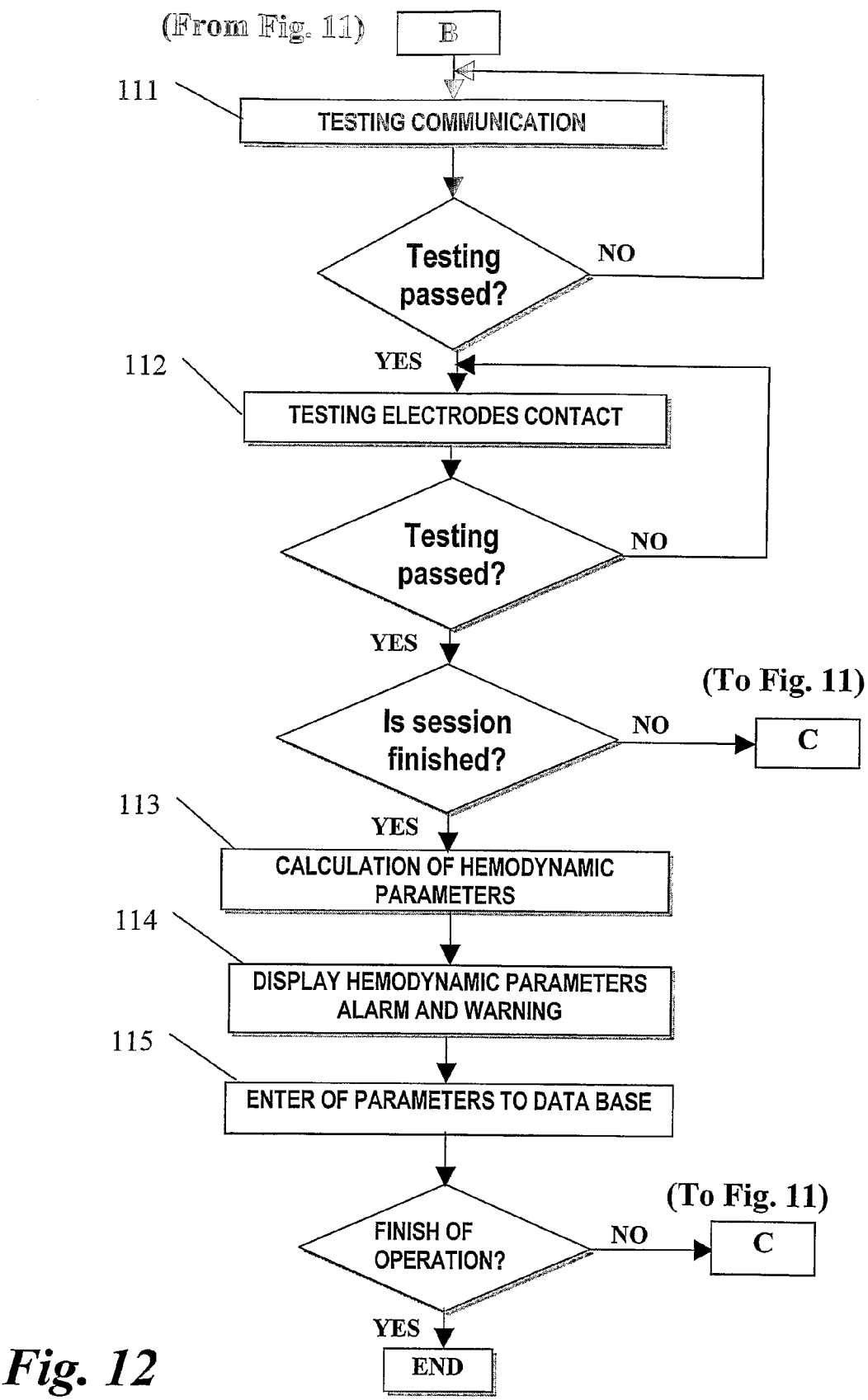

FIGS. 10-12 are flowcharts illustrating an algorithm in accordance with which the apparatus functions according to a preferred embodiment of the present invention.

The apparatus performs the following tests: in step 100 a communication test is performed to determine if there is communication between the microcontroller 30 and the computer system 37 (see FIG. 5), in step 101 the operation of the ECG front end 34 (see FIG. 5) is tested, and in step 102 the electrical impedance measuring circuit is tested. If all the tests 100-102 are successfully passed, the control passes to step 103, otherwise, the computer system 37 displays a corresponding alarm and performs the failed tests continuously until the reason for the malfunctioning is overcome.

In step 103, the operator enters information about the patient and parameters of the measurement process. If the entered data is correct (i.e., the patient information is properly entered), the control is passed to step 104, otherwise, the computer system 37 prompts a message to the operator to correct the entered data.

In step 104, the computer system 37 displays ECG waveforms for several ECG leads, and the operator selects an optimal ECG lead.

In step 105 (FIG. 11), the gain value of the PGA 31 (see FIG. 9) is defined by carrying out the following steps:
1. The microcontroller 30 sets a preliminary gain for the PGA 31 which corresponds to a minimal value;
2. The values of Ua are obtained sequentially for all EBI leads (as shown in FIG. 9) and the microcontroller 30 stores the values in memory; and
3. The microcontroller 30 calculates an optimal value of gain for PGA 31 for each EBI lead and stores the values in memory.

In step 106, the resistance of each EBI lead is determined and analyzed by performing the following steps:
1. The microcontroller 30 sequentially sets the gain of the PGA 31 to the values that were previously stored in its memory for each EBI lead, and obtains accurate values of Ua utilizing the scheme shown in FIG. 9;
2. The microcontroller 30 corrects the gain values utilizing the obtained values of Ua;
3. The conversion block 75 is used to calculate the values of R1-R4, by solving equations 1-4 for EBI leads 1-4 and equation 5 for EBI leads RA, LA, RL, LL, and F;
4. The computer system 37 (see FIG. 5) displays the obtained resistance values, and, if some of the resistance values are off range of allowable values, it displays a warning; and
5. The computer system 37 stores the values of R that were obtained for future use.

In step 107, the operation of the impedance measurement apparatus begins. First, the apparatus determines the values of Ua for all EBI leads by the operation of the microcontroller 30, which sequentially sets the gain of the PGA 31 to the values that were previously, and obtains the values of Ua accordingly utilizing the implementation shown in FIG. 9.

In step 108, the values of R and ΔR are determined for all EBI leads by performing the following steps:
1. The conversion block 75 calculates the values of R1-R4, by solving equations 1-4 for EBI leads 1-4 and equation 5 for EBI leads RA, LA, RL, LL, and F; and
2. The substractor 74 determines the values of ΔR for all EBI leads.

In step 109, the apparatus processes the ECG signal. The processing of the ECG signal includes filtration of ECG waveform, detection of QRS complexes and calculation of the heart rate.

In step 110, the computer system 37 displays the ECG signal and the ΔR waveforms.

In steps 111 and 112 (FIG. 12), the apparatus performs a communication test between the microcontroller 30 and the computer system 37, and a test of the electrode contacts of the electrodes 12-21. If all the tests are successfully passed, the control is passed to step 113, otherwise, the computer system 37 displays a corresponding alarm and repeats the failed test continuously until the reason for malfunctioning is overcome. The session continues until the apparatus processes a fixed number, for example 20, of the cardiac cycles. If the apparatus has processed the fixed number of cycles the session is finished, otherwise, the cycle continues.

In step 113, the hemodynamic parameters are calculated, and in step 114, the computer system 37 displays the calculated hemodynamic parameters, for example, stroke volume.

In step 115, the hemodynamic parameters and the patient information is entered to the database located in the computer system 37 or in another remote computer, after which the apparatus operation ends.

The above examples and description have of course been provided only for the purpose of illustration, and are not intended to limit the invention in any way. As will be appreciated by the skilled person, the invention can be carried out in a great variety of ways, employing techniques different from those described above, all without exceeding the scope of the invention.

The invention claimed is:

1. A method for measuring the electrical impedance of sections of a living body utilizing an electrical model based on the distribution of electrical currents through said sections, comprising:
   a) applying at least four limb electrodes to a right arm, a left arm, a right leg and a left leg of the living body, such that at least one of said limb electrodes is applied to each of the right arm, the left arm, the right leg, and the left leg;
   b) applying at least four trunk electrodes to a trunk area of the measured body, such that at least one of said trunk electrodes is applied to each of a superior part of a right side of the trunk, a inferior part of the right side of the trunk, the superior part of left side of the trunk, and the inferior part of the left side of the trunk;
   c) performing at least six of the following measurements, the measurements being any combination of six measurements selected from the measurement techniques of:
      c.1) measuring the voltage over a right pair of trunk electrodes applied to superior and inferior parts of the right side of the trunk, and the voltage over a left pair of trunk electrodes applied to superior and inferior parts of the left side of the trunk, where said voltages are measured in response to an excitation current applied via limb electrodes applied to the left leg and to the left arm;
      c.2) measuring the voltage over a right pair of trunk electrodes applied to superior and inferior parts of the right side of the trunk, and the voltage over a left pair of trunk electrodes applied to superior and inferior parts of the left side of the trunk, where said voltages are measured in response to an excitation current applied via limb electrodes applied to the right leg and to the right arm;
      c.3) measuring the voltage over a superior pair of trunk electrodes applied to the right and to the left sides of a superior part of the trunk, and the voltage over an inferior pair of trunk electrodes applied to the right and to the left sides of an inferior part of the trunk, said voltages are measured in response to an excitation current applied via limb electrodes applied to the right leg and to the left leg; and
      c.4) measuring the voltage over a superior pair of trunk electrodes applied to the right and to the left sides of a superior part of the of the trunk, and over an inferior pair of trunk electrodes applied to the right and to the left sides of an inferior part of the trunk, said voltages are measured in response to an excitation current applied via limb electrodes applied to the right arm and to the left arm; and
   d) computing the electrical impedance between said pairs of trunk and limb electrodes utilizing the measured voltages by said at least six measurements according to said electrical model;
   wherein the at least six measurements are performed by carrying out the following steps:
      i) selecting a pair of limb electrodes from the at least four limb electrodes applied to the right arm, the left arm, left leg and right leg to be used as excitation electrodes and a pair of trunk electrodes from the at least four trunk electrodes applied to the trunk area to be used as sensing electrodes;
      ii) continuously generating digital signal corresponding to a sinusoidal signal;
      iii) converting said digital signal into an analog signal;
      iv) applying a constant electrical current, the magnitude of which is proportional to the magnitude of said analog signal, via said excitation electrodes;
      v) amplifying the voltage over said sensing electrodes;
      vi) converting said amplified voltage into a digital signal; wherein said digital signal is used for the computation of the impedance signal; and
      vii) processing the amplified voltage converted into a digital signal and computing an active component of the impedance and the changes of said component, by performing the following steps:
         a) splitting said digital signal into wave-packets, where each wave-packet includes a complete number cycles of said signal;
         b) multiplying said wave-packets by a digital sinusoidal waveform with the same frequency and phase as the signal cycles in the wave-packets;
         c) summing the results of the multiplication of a wave-packet by said digital sinusoidal waveform;
         d) storing the summation results in a memory;
         e) calculating the measured resistance by utilizing said summation results and the electrical model;
         f) filtering said measured resistance by a low-pass-filter to obtain the mean value of said measured resistance; and
         g) subtracting said mean value from said measured resistance to obtain the changes of said measured resistance and basal resistance;
   wherein the multiplication of the wave-packet comprises multiplying each wave-packets signal by itself, thereby raising it to the second power, to obtain the impedance value and it changes.

2. The method according to claim 1, wherein the at least four limb electrodes applied to the arms and legs are applied to the extremities of said arms and legs.

3. The method according to claim 1, wherein the at least four trunk electrodes applied to the trunk area are applied to the superior and inferior parts of left and right sides of the chest.

4. The method according to claim 1, further comprising providing a peripheral blood flow parameter electrode applied to a superior head section for measuring peripheral blood flow parameters utilizing a bipolar electrode configuration.

5. The method according to claim 4, further comprising providing an additional electrode applied to the superior head section in the vicinity of the peripheral blood flow parameter electrode for measuring peripheral blood flow parameters utilizing a tetrapolar electrode configuration.

6. The method according to claim 1, further comprising applying at least four additional limb electrodes, wherein at least one of said additional limb electrodes is applied to each of the right arm, the left arm, the right leg, and the left leg and placed in the vicinity of the limb electrode that receives an excitation current, for measuring peripheral blood flow parameters utilizing a tetrapolar electrode configuration.

7. The method according to claim 1, wherein only the active component of the impedance is computed.

8. The method according to claim 1, further comprising measuring electrical impedances associated with parameters of peripheral blood flow as follows:
  a) obtaining the electrical impedance associated with the right arm by measuring the voltage obtained via the limb electrode applied to said arm and the trunk electrode applied to the superior part of the right side of the trunk, where said voltage is being responsive to an excitation current applied via said limb and trunk electrodes;
  b) obtaining the electrical impedance associated with blood flow parameters of the left arm by measuring the voltage obtained via the limb electrode applied to said arm and the trunk electrode applied to the superior part of the left side of the trunk, where said voltage is being responsive to an excitation current applied via said limb and trunk electrodes;
  c) obtaining the electrical impedance associated with blood flow parameters of the right leg by measuring the voltage obtained via the limb electrode applied to said leg and the trunk electrode applied to the inferior part of the right side of the trunk, where said voltage is being responsive to an excitation current applied via said limb and trunk electrodes; and
  d) obtaining the electrical impedance associated with flow parameters of the left leg by measuring the voltage obtained via the limb electrode applied to said leg and the trunk electrode applied to the inferior part of the left trunk, where said voltage is being responsive to an excitation current applied via said limb and trunk electrodes.

9. The method according to claim 1, further comprising providing an additional pair of limb electrodes applied to a finger of the living body for measuring electrical impedance associated with parameters of peripheral blood flow by utilizing a bipolar electrode configuration.

10. The method according to claim 1, further comprising filtering the analog signal by a low-pass-filter.

11. The method according to claim 1, further comprising filtering the amplified signal by a high-pass-filter.

12. The method according to claim 1, further comprising providing means for measuring ECG signals via at least three electrodes.

13. The method according to claim 1, wherein the electrical current is an alternating electrical current.

14. The method according to claim 1, wherein the electrical current is produced by a current source.

15. The method according to claim 1, wherein impedance measurements are used for assessing pulmonary systematic and peripheral blood flow and calculating hemodynamic parameters of the probed sections.

16. The method according to claim 1, wherein electrical impedances associated with aortic flow, pulmonary arterial flow, and pulmonary flow parameters, are obtained by carrying out the following measurements:
  a) measuring a voltage obtained via a right pair of electrodes applied to the superior and inferior parts of the right side of the trunk, $U1$, and a voltage obtained via a left pair of electrodes applied to the superior and inferior parts of the left side of the trunk, $U12$, in response to an excitation current $Is$ applied through electrodes applied to the left arm and to the left leg;
  b) measuring a voltage obtained via a left pair of electrodes applied to the superior and inferior parts of the left trunk, $U2$, and a voltage obtained via a right pair of electrodes applied to the superior and inferior parts of the right trunk, $U21$, in response to an excitation current $Is$ applied through electrodes applied to the right arm and to the right leg;
  c) measuring a voltage obtained by a superior pair of electrodes applied to the right and left parts of the superior trunk, $U3$, and by an inferior pair of electrodes applied to the right and left parts of the inferior trunk, $U34$, in response to an excitation current $Is$ applied through electrodes applied to the right leg and to the left leg, and
  d) computing the impedance signals:

$R1=(U1*U2-U12*U21)/(Is*(U2-U12))$ between said right pair of electrodes, $R2=(U1*U2-U12*U21)/(Is*(U1-U21))$ between said left pair of electrodes, $R3=U3*(R1+R2)/(Is*(R1+R2)-U3+U34)$ between said superior pair of electrodes, and $R4=(U34*(R1+R2))/(U3-U34)$ between said inferior pair of electrodes.

* * * * *